(12) United States Patent
Haas et al.

(10) Patent No.: US 11,623,106 B2
(45) Date of Patent: *Apr. 11, 2023

(54) SYSTEMS, METHODS AND DEVICES FOR AUTOMATED TARGET VOLUME GENERATION

(71) Applicant: Siemens Healthineers International AG, Steinhausen (CH)

(72) Inventors: Benjamin Haas, Brittnau (CH); Marco Lessard, Trois Rivieres (CA); Jonas Honegger, Zurich (CH); Thomas Coradi, Lenzburg (CH); Tobias Gass, Vogelsang AG (CH); Tomasz Morgas, Henderson, NV (US)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 17 days.

This patent is subject to a terminal disclaimer.

(21) Appl. No.: 17/146,775

(22) Filed: Jan. 12, 2021

(65) Prior Publication Data

US 2021/0138265 A1 May 13, 2021

Related U.S. Application Data

(63) Continuation of application No. 16/144,253, filed on Sep. 27, 2018, now Pat. No. 10,918,885.

(51) Int. Cl.
*G06T 7/00* (2017.01)
*A61N 5/10* (2006.01)
(Continued)

(52) U.S. Cl.
CPC .......... *A61N 5/1031* (2013.01); *A61B 6/466* (2013.01); *G06T 7/0014* (2013.01); *G06T 7/149* (2017.01);
(Continued)

(58) Field of Classification Search
CPC . G06T 2207/10081; G06T 2207/30004; G06T 7/337; G06T 7/30; G06T 7/33;
(Continued)

(56) References Cited

U.S. PATENT DOCUMENTS

| | | |
|---|---|---|
| 6,829,382 B2 | 12/2004 | Lee |
| 7,567,694 B2 | 7/2009 | Lu et al. |

(Continued)

FOREIGN PATENT DOCUMENTS

| | | |
|---|---|---|
| CN | 101267858 A | 9/2008 |
| CN | 107072628 A | 8/2017 |

(Continued)

OTHER PUBLICATIONS

Ramadaan et al., "Validation of Varian's SmartAdapt deformable image registration algorithm for clinical application," Radiation Oncology, DOI 10.1186/s13014-015-0372-1, 2015.

(Continued)

*Primary Examiner* — Li Liu
(74) *Attorney, Agent, or Firm* — SGPatents PLLC

(57) ABSTRACT

Systems and method for automatically generating structures, such as target volumes, in a treatment image using structure-guided deformation to propagate the structures from a planning image onto the subsequently acquired treatment image.

6 Claims, 14 Drawing Sheets

(51) Int. Cl.
  *G06T 7/38* (2017.01)
  *G06T 7/149* (2017.01)
  *G06T 7/33* (2017.01)
  *A61B 6/00* (2006.01)
  *G06T 7/12* (2017.01)
  *A61B 6/03* (2006.01)

(52) U.S. Cl.
  CPC ............... *G06T 7/337* (2017.01); *G06T 7/38* (2017.01); *A61B 6/03* (2013.01); *G06T 7/12* (2017.01); *G06T 2207/30004* (2013.01)

(58) Field of Classification Search
  CPC ............ G06T 7/0014; G06T 7/12; G06T 2207/10072; G06T 2207/10116; G06T 7/149; G06T 7/174; G06T 7/38; G06T 7/11; G06V 2201/03; G06V 10/754; G06V 10/24
  See application file for complete search history.

(56) References Cited

U.S. PATENT DOCUMENTS

| | | | |
|---|---|---|---|
| 9,053,541 B2* | 6/2015 | Piper | G06T 7/33 |
| 9,245,336 B2 | 1/2016 | Mallya et al. | |
| 9,336,591 B2 | 5/2016 | Mallya et al. | |
| 9,418,427 B2 | 8/2016 | Piper | |
| 9,679,373 B2* | 6/2017 | Vilsmeier | G06T 7/0012 |
| 9,743,896 B2 | 8/2017 | Averbuch | |
| 9,757,588 B2 | 9/2017 | Kaus et al. | |
| 9,818,189 B2* | 11/2017 | Dahlqvist Leinhard | G06T 7/11 |
| 9,962,086 B2* | 5/2018 | Dabbah | A61B 6/5235 |
| 10,058,714 B2* | 8/2018 | Hårdemark | A61N 5/1039 |
| 10,635,930 B2* | 4/2020 | Geiger | G06V 20/64 |
| 2006/0074292 A1 | 4/2006 | Thomson et al. | |
| 2007/0116381 A1 | 5/2007 | Khamene | |
| 2009/0087124 A1 | 4/2009 | Nord et al. | |
| 2011/0103551 A1* | 5/2011 | Bal | A61N 5/103 378/65 |
| 2011/0317896 A1 | 12/2011 | Huber et al. | |
| 2013/0004034 A1 | 1/2013 | Tome et al. | |
| 2013/0259335 A1 | 10/2013 | Mallya et al. | |
| 2013/0329980 A1 | 12/2013 | Pekar et al. | |
| 2014/0049555 A1 | 2/2014 | Bzdusek et al. | |
| 2014/0201670 A1 | 7/2014 | Mallya et al. | |
| 2015/0174428 A1 | 6/2015 | Bzdusek et al. | |
| 2015/0363080 A1 | 12/2015 | Buelow et al. | |
| 2016/0019680 A1 | 1/2016 | Kabus | |
| 2016/0206263 A1 | 7/2016 | Ruppertshofen et al. | |
| 2016/0300120 A1 | 10/2016 | Haas et al. | |
| 2018/0314906 A1 | 11/2018 | Yang et al. | |
| 2019/0251693 A1 | 8/2019 | Buerger et al. | |

FOREIGN PATENT DOCUMENTS

| | | |
|---|---|---|
| WO | WO 2010/148250 A2 | 12/2010 |
| WO | WO 2015/085252 A1 | 6/2015 |

OTHER PUBLICATIONS

Koenig et al. "Deformable image registration for adaptive radiotherapy with guaranteed local rigidity constraints," Radiation Oncology, DOI 10.1186/s13014-016-0697-4, 2016.

Murphy et al., "How does CT image noise affect 3D deformable image registration for image-guided radiotherapy planning?" Med. Phys., vol. 35, No. 3, Mar. 2008, pp. 1145-1153.

Robertson et al., "Deformable mesh registration for the validation of automatic target localization algorithms," Med. Phys., vol. 40, No. 7, Jul. 2013.

Pukala et al., "Benchmarking of five commercial deformable image registration algorithms for head and neck patients," Journal of Applied Clinical Medical Physics, vol. 17, No. 3, 2016, pp. 25-40.

Wijesooriya et al., "Quantifying the accuracy of automated structure segmentation in 4D CT images using a deformable image registration algorithm," Med. Phys., vol. 35, No. 4, Apr. 2008, pp. 1251-1260.

Zhu et al., "Deformable Image Registration with Inclusion of Autodetected Homologous Tissue Features," The Scientific World Journal, vol. 2012, Article ID 913693, 8 pages, DOI:10.1100/2012/913693.

Patil et al., "Automatic deformable MR-ultrasound registration for image-guided neurosurgery," Global Journal of Advanced Engineering Technologies, vol. 5, Issue 2, 2016, pp. 113-117.

Yang et al., "Contour Propagation Using Feature-Based Deformable Registration for Lung Cancer," BioMed Research International, vol. 2013, Article ID 701514, 8 pages, DOI 10.1155/2013/701514.

Gu et al., "A contour-guided deformable image registration algorithm for adaptive radiotherapy," Physics in Medicine and Biology, Mar. 2013, DOI 10.1088/0031-9155/58/6/1889.

Costa et al., "Automatic segmentation of the bladder using deformable models," IEEE International Symposium on Biomedical Imaging: From Nano to Macro, 2007, DOI 10.1109/ISBI.2007.356999.

Extended European Search Report and European Search Opinion dated Mar. 11, 2020, in European Patent Application No. 19198653.8.

Murphy et al., "A method to estimate the effect of deformable image registration uncertainties on daily dose mapping," Medical Physics 39.2 (2012): pp. 573-580.

Office Action dated Sep. 21, 2022, in Chinese Patent Application No. 201910916439.1.

* cited by examiner

SYSTEMS, METHODS AND DEVICES FOR AUTOMATED TARGET VOLUME GENERATION

FIELD

The present disclosure relates generally to systems, methods, and devices for generating structures in an image, and more particularly, to structure-guided deformable image registration used for target volume generation in a treatment image.

BACKGROUND

Radiation therapy involves medical procedures that use external radiation beams to treat pathological anatomies (tumors, lesions, vascular malformations, nerve disorders, etc.) by delivering prescribed doses of radiation (X-rays, gamma rays, electrons, protons, and/or ions) to the pathological anatomy, while minimizing radiation exposure to the surrounding tissue and critical anatomical structures.

In general, radiation therapy treatments consist of several phases. First, a precise three-dimensional (3D) map of the anatomical structures in the area of interest (head, body, etc.) is constructed using any one of (or combinations thereof) a computed tomography (CT), cone-beam CBCT, magnetic resonance imaging (MRI), positron emission tomography (PET), 3D rotational angiography (3DRA), or ultrasound techniques. This determines the exact coordinates of the target within the anatomical structure, namely, locates the tumor or abnormality within the body and defines its exact shape and size. Second, a motion path for the radiation beam is computed to deliver a dose distribution that the surgeon finds acceptable, considering a variety of medical constraints. During this phase, a team of specialists develop a treatment plan using special computer software to optimally irradiate the tumor and minimize dose to the surrounding normal tissue by designing beams of radiation to converge on the target area from different angles and planes. Third, the radiation treatment plan is executed. During this phase, the radiation dose is delivered to the patient according to the prescribed treatment plan. Generally, a treatment plan is delivered to the patient over a series of radiation treatments referred to as fractions.

There are many factors that can contribute to differences between the prescribed radiation dose distribution and the actual dose delivered (i.e., the actual dose delivered to the target during the radiation treatment). One such factor is uncertainty in the patient's position in the radiation therapy system. Other factors involve uncertainty that is introduced by changes that can occur during the patient's treatment. Such changes can include random errors, such as small differences in a patient's setup position. Other sources are attributable to physiological changes that might occur if a patient's tumor regresses or if the patient loses weight during therapy. Another category of uncertainty includes motion. Motion can potentially overlap with either of the categories as some motion might be more random and unpredictable, whereas other motion can be more regular.

These anatomical and physiological changes can cause the target volumes and surrounding anatomical structures and organs to move and change in size and shape during the therapy. As such, continuing to follow the initial treatment plan may result in an actual received dose distribution that differs from the planned distribution, and thus reduced doses to target volumes and/or increased doses to organs at risk (OARs). Adapting the treatment plan, namely, making modifications to the initial treatment plan to match the new location and shape of the target volume and surrounding anatomical structures based on subsequently acquired image data is one way to rectify this problem.

Adaptive radiation therapy is a process by which, using subsequent images, an original treatment plan can be adjusted to counteract these anatomical changes. For example, in an off-line adaptive therapy process, during each treatment fraction, a new image (CT image, for example) of the patient is acquired before or after each of the fractions and the images are evaluated to determine multi-day locations of the target volumes. Based on this, a new plan can be developed to better reflect the range of motion of the target volumes. Adaptive radiation therapy can also allow for recalculating the delivered dose after each fraction and accumulate these doses utilizing image deformation techniques during the accumulation to account for internal motions. The calculated doses can then be compared to the planned dose, and if any discrepancies are noted, subsequent fractions can be modified to account for the changes. In an on-line adaptive therapy process, the radiation therapy system can be used prior to treatment to validate or adjust the patient's setup for the treatment delivery. The imaging system can thus be used to concurrently modify the treatment delivery to reflect the changes in the patient's anatomy.

As the impact of anatomical changes and/or patient positioning depends on the individual patient and the details of the treatment plan, no general rules are applied to indicate when re-imaging and re-planning is to be done. Instead, in-treatment imaging is reviewed one or multiple times during a treatment regimen by medical personnel to verify reproducibility of patient positioning and assess anatomical changes to determine if re-planning is necessary. Subsequently, the initial treatment plan is copied onto the new image, and the dosimetric changes are assessed. If these dosimetric changes show that the target coverage or that OAR sparing may be compromised, the relevant anatomical structures are re-contoured by the medical personnel and a new treatment plan is created.

The workload involved in such adaptive re-planning can be complex and time consuming, as this involves the need to generate a new target volume and thus delineation (contouring) or segmentation of the tissue of interest and anatomical structures for the patient from the latest image data. The new target volume needs to be anatomically consistent with the initially defined target but adapted to the position of the anatomy at the time of fraction delivery. Re-contouring of all relevant structures is, however, time consuming.

Deformable image registration (DIR) has been used to quantify the detected anatomical changes and to automate the re-contouring of anatomical structures after an anatomical change has been observed, by propagating contours in the initial image to contours in the latest image data. The propagation is done by correlating locations of a patient's anatomy or physiology across the multiple images while accounting for non-rigid changes in the anatomy between images, phases and times. In adaptive radiation therapy, deformable image registration (DIR) is often conducted between the planning image (CT image, for example) and the treatment image (CT image, for example) to generate a deformation vector field (DVF) for dose accumulation and contour propagation. The deformation vector field (DVF) indicates the displacement transformations to align the planning image with the treatment image. Thus, the deformation vector field (DVF) spatially maps the planning image to the treatment image.

Using a deformation vector field (DVF) to map the planning image contours from the planning image to the treatment image introduces risks, however, in that any errors in the deformation vector field (DVF) may result in auto-propagated contours on the treatment image that contain relatively large errors. Errors in the deformation vector field (DVF) may be caused, for example, by severe deformations which are difficult to map accurately, or by image artifacts, or by features that appear in only one image, and/or by propagating features that possess varying deformation properties using deformable registration algorithms that do not take that into consideration.

As such, structures in the planning image that exhibit a lot of movement, such as the bladder, rectum, and uterus, for example, deform significantly from day to day, and thus are not good candidates for propagation. Also, structures that do not exhibit homogenous deformation properties, namely, structures that have different parts that deform differently, such as lymph nodes for example, which deform more rigidly around the bones and more elastically near soft tissue organs, are also not good candidates for propagation with a standard deformation vector field due to the assumption that the structure has homogenous deformation properties.

One way to address the errors in the contour mapping is to allow the medical personnel to view the propagated contour superimposed on the treatment image and manually edit the contour. However, this approach only corrects the contour but not the deformation vector field (DVF) that was the source of the erroneous contour. This can generate problems during the course of treatment, since other aspects of radiation therapy, such as the determination of dose accumulation, for example, depend directly on the deformation vector field (DVF) rather than the contours. Further, additional manual editing of already propagated structures slows down the re-planning process.

There is a need therefore for a suitable transformation (i.e., deformation vector field (DVF)) that considers the large motions of structures as well as the different deformation properties of the propagated structures.

SUMMARY

Embodiments of the disclosed subject matter enable the generation of structures (contours) in a treatment image using deformable registration techniques that consider the large motions of different structures, as well as the different deformation properties of the structures.

Embodiments of the disclosed subject matter enable the automatic generation of one or more structures in a treatment image and/or any other image to be used in adaptive radiation therapy or otherwise, which includes all structures from the planning image.

Embodiments of the disclosed subject matter enable the generation of one or more deformation vector fields (DVF) (i.e., displacement transformations) that allow for the automatic propagation of structures/contours from the pre-treatment (planning, for example) image to a subsequent image (treatment session, for example) that considers the large motions of structures as well as the different deformation properties of the propagated structures.

Embodiments of the disclosed subject matter enable performing a treatment session on a subject based on image data of the subsequent image, and/or determining a treatment plan for the treatment session based on the image data of the subsequent image.

Embodiments of the disclosed subject matter further enable determining whether re-planning is necessary using a treatment image which includes contours automatically generated using a structure-guided deformable registration algorithm.

Embodiments of the disclosed subject matter further enable generating structures in a current image by applying deformable registration between the current image including a structure and a previously generated image that includes the structure and one or more other structures and applying deformable registration between the two images to propagate the one or more structures from the previously generated image to the current image using a structure-guided deformable registration algorithm.

In one or more embodiments, a method includes determining a registration transformation that is based at least on a structure-guided deformable registration.

In one or more embodiments, a method includes incorporating so-called influencer structures as inputs into the deformable registration algorithm.

In one or more embodiments, the so-called influencer structures guide the deformable registration process.

In one or more embodiments, the guiding is realized by incorporating a constraint in the deformable registration algorithm to enable matching of influencer structures present in a planning image with the same influencer structures present in a subsequent treatment image.

In one or more embodiments, a method includes incorporating local rigidity as a constraint in the deformable registration algorithm to enable locally rigid deforming structures to be accurately propagated.

In one or more embodiments, a method is disclosed for generating structures in an image, comprising: obtaining a first image including a first set of structures and a second set of structures, the first and second set of structures being located at respective first locations in the first image; obtaining a second image including the second set of structures, the second set of structures being located at a second location in the second image, the second location being different from the first location of the second set of structures in the first image; and propagating the first set of structures from the first image to the second image based on image registration that is guided by the second set of structures.

In one or more embodiments, the second set of structures can include structures that affect/influence one or more structures in the first set of structures.

In one or more embodiments, the image registration is a deformable image registration.

In one or more embodiments, the guiding is realized by incorporating a constraint in the deformable registration algorithm to enable matching of the second set of structures present in the first image with the same second set of structures present in the second image.

In one or more embodiments, the generating includes applying a structure-guided deformable registration algorithm that enables: obtaining one or more deformation vector fields (DVFs) between the first and second images; and using the one or more deformation vector fields (DVFs) to propagate the first set of structures from the first image to the second image.

In one or more embodiments, the obtaining includes relating the first set of structures from the first image to the second image to create first set of structures in the second image; modifying the first set of structures in the second image based on the second set of structures in the second image; generating one or more revised deformation vector fields (DVFs) based on the modifying; and applying the one or more revised deformation vector fields (DVFs) to relate the first set of structures from the first image to the second image to generate a revised first set of structures in the second image.

In one or more embodiments, the deformable registration algorithm further enables partially rigid deformations of one or more structures within the first set of structures.

In one or more embodiments, the first set of structures can include one or more target volumes and one or more anatomical structures of interest, and the second set of structures includes one or more anatomical influencer structures.

In one or more embodiments, the anatomical influencer structures can include anatomical structures that influence one of a shape, size, or location of the one or more target volumes.

In one or more embodiments, a system is disclosed that enables the performing of any of the processes disclosed herewithin.

In one or more embodiments, there are provided a non-transitory computer-readable storage medium upon which is embodied a sequence of programmed instructions for the generation of day to day treatment images to be used in adaptive radiation therapy or otherwise using a structure-guided deformable registration process, and a computer processing system that executes the sequence of programmed instructions embodied on the computer-readable storage medium. Execution of the sequence of programmed instructions can cause the computer processing system to generate one or more deformable registration vector fields that accurately and automatically propagate all structures in a previously obtained image to a later, subsequently obtained image to be used in adaptive therapy or any other radiation treatment systems and processes.

Objects and advantages of embodiments of the disclosed subject matter will become apparent from the following description when considered in conjunction with the accompanying drawings.

BRIEF DESCRIPTION OF DRAWINGS

Embodiments will hereinafter be described with reference to the accompanying drawings, which have not necessarily been drawn to scale. These drawings are for illustration purposes only and are not intended to limit the scope of the present disclosure in any way. Where applicable, some features may not be illustrated to assist in the illustration and description of underlying features. Throughout the figures, like reference numerals denote like elements. As used herein, various embodiments can mean one, some, or all embodiments.

DETAILED DESCRIPTION

Figure 1:
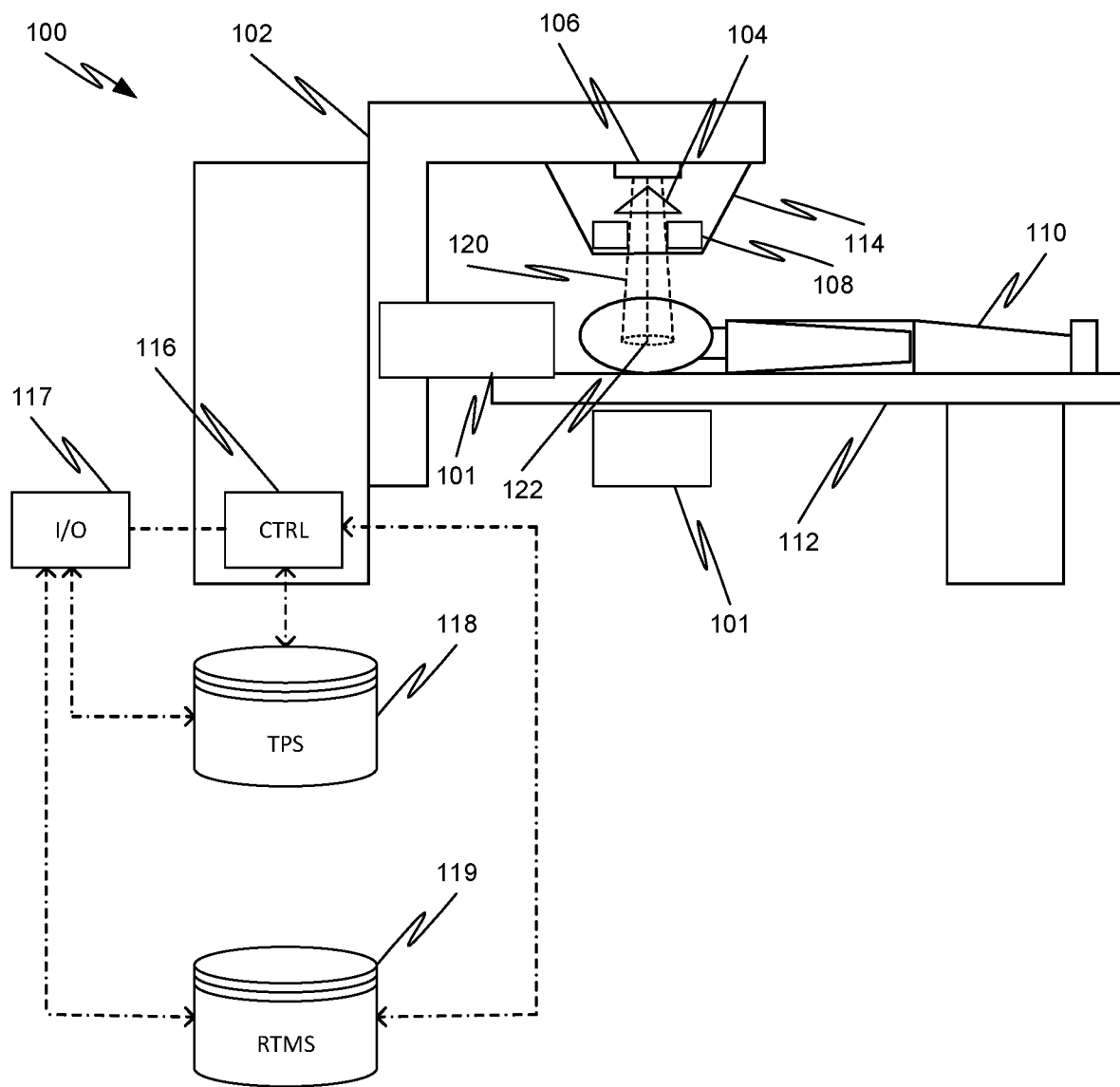
FIG. 1 is a simplified schematic diagram of a radiation therapy system, according to various embodiments of the disclosed subject matter.

Referring to FIG. 1, an exemplary radiation therapy system 100 is shown that can be used in adaptive radiation therapy. The therapy system 100 can provide radiation to a patient 110 positioned on a treatment couch 112 and can allow for the implementation of various radiation dose verification protocols. The radiation therapy can include photon-based radiation therapy, particle therapy, electron beam therapy, or any other type of treatment therapy.

In an embodiment, the radiation therapy system 100 can include a radiation treatment device 101 such as, but not limited to, a LINAC operable to generate one or more beams of megavolt (MV) X-ray radiation for treatment. The LINAC may also be operable to generate one or more beams of kilovolt (kV) X-ray radiation, for example, for patient imaging. The system 100 has a gantry 102 supporting a radiation treatment head 114 with one or more radiation sources 106 and various beam modulation elements, such as, but not limited to, flattening filter 104 and collimating components 108. The collimating components 108 can include, for example, a multi-leaf collimator (MLC), upper and lower jaws, and/or other collimating elements. The collimating components 108 and/or the flattening filter 104 can be positioned within the radiation beam path by respective actuators (not shown), which can be controlled by controller 116.

The gantry 102 can be a ring gantry (i.e., it extends through a full 360° arc to create a complete ring or circle), but other types of mounting arrangements may also be employed. For example, a static beam, or a C-type, partial ring gantry, or robotic arm can be used. Any other framework capable of positioning the treatment head 114 at various rotational and/or axial positions relative to the patient 110 may also be used.

In an embodiment, the radiation therapy device is a MV energy intensity modulated radiation therapy (IMRT) device. The intensity profiles in such a system are tailored to the treatment requirements of the individual patient. The IMRT fields are delivered with MLC 108, which can be a computer-controlled mechanical beam shaping device attached to the head 114 and includes an assembly of metal fingers or leaves. For each beam direction, the optimized intensity profile is realized by sequential delivery of various subfields with optimized shapes and weights. From one subfield to the next, the leaves may move with the radiation beam on (i.e., dynamic multi-leaf collimation (DMLC)) or with the radiation beam off (i.e., segmented multi-leaf collimation (SMLC)).

Alternatively, or additionally, the radiation therapy device 101 can be a tomotherapy device where intensity modulation is achieved with a binary collimator (not shown) which opens and closes under computer control (e.g., control 116). As the gantry 102 continuously rotates around the patient 110, the exposure time of a small width of the beam can be adjusted with opening and closing of the binary collimator, allowing radiation 120 to be directed to a portion of the body of the patient 110 and delivered to a region of interest 122 through the most desirable directions and locations of the patient 110. The region of interest is a two-dimensional area and/or a three-dimensional volume that is desired to receive the radiation and it may be referred to as a target or target region or target volume. Another type of region of interest is a region of risk. If a portion includes a region of risk, the radiation is diverted from the region of risk. The patient 110 may have more than one target region that needs to receive radiation therapy.

Alternatively, or additionally, the radiation therapy device can be a helical tomotherapy device, or a simplified intensity modulated arc therapy (SIMAT) device, a volumetric modulated arc therapy (VMAT) device, or a volumetric high-definition (or hyperarc) therapy (HDRT). In effect, any type of IMRT device can be employed as the radiation therapy device 101 of system 100, and can also include an on-board volumetric imaging, which can be used to generate in-treatment image data generated during a treatment session.

For example, embodiments of the disclosed subject matter can be applied to image-guided radiation therapy (IGRT) devices, which uses cross-sectional images of a patient's internal anatomy taken during the radiation therapy treatment session (i.e., in-treatment images) to provide information about the patient's position. Frequent two or three-dimensional imaging during the radiation treatment is used to direct the therapeutic radiation utilizing the imaging coordinates of the actual radiation treatment plan. This ensures that the patient is localized in the radiation treatment system in the same position as planned, and that the patient is properly aligned during the treatment. Although, the IGRT process involves conformal radiation treatment guided by specialized imaging tests taken during the planning phase, it does rely on the imaging modalities from the planning process as the reference coordinates for localizing the patient 110 during treatment. Thus, associated with each image-guided radiation therapy system is an imaging system to provide in-treatment images that are used to set-up the radiation delivery procedure.

In-treatment images can include one or more two or three-dimensional images (typically X-ray) acquired at one or more different points during treatment. There are a variety of ways to acquire in-treatment images. In certain approaches, distinct independent imaging systems and/or imaging methods are used for acquiring pre-treatment and in-treatment images, respectively. For example, a 3D IGRT could include localization of a cone-beam computed tomography (CBCT) dataset with a planning computed tomography (CT) dataset, and a 2D IGRT could include matching planar kilovoltage (kV) radiographs or megavoltage (MV) images with digital reconstructed radiographs (DRRs) obtained from the planning CT.

Another approach is to use portal imaging systems. In portal imaging systems, a detector is placed opposite the therapeutic radiation source to image the patient for setup and in-treatment images. Another approach is X-ray tomosynthesis which is an in-treatment imaging modality for use in conjunction with radiation treatment systems.

Alternatively, the system 100 can include a kilovoltage or a megavoltage detector operable to receive the radiation beam 120. The radiation therapy device 101 and the detector can operate as a computed tomography (CT) system to generate CT images of the patient. The images can illustrate the patient's body tissues, organs, bone, soft tissues, blood vessels, etc. Alternatively, the radiation therapy device can operate as an MRI device to generate images of the patient.

Each type of radiation therapy device can be accompanied by a corresponding radiation plan and radiation delivery procedure.

The controller 116, which can be, but is not limited to, a graphics processing unit (GPU), can include a computer with appropriate hardware such as a processor, and an operating system for running various software programs and/or communication applications. The controller 116 can include software programs that operate to communicate with the radiation therapy device 101, which software programs are operable to receive data from external software programs and hardware. The computer can also include any suitable input/output (I/O) devices 117, which can be adapted to allow communication between controller 116 and a user of the radiation therapy system 100, e.g., medical personnel. For example, the controller can be provided with I/O interfaces, storage devices, memory, keyboard, mouse, monitor, printers, scanner, etc.

Alternatively, or additionally, the I/O devices 117 can provide access to a network (not shown) for transmitting data between controller 116 and remote systems. For example, the controller 116 can be networked via I/O 117 with other computers and radiation therapy systems. The radiation therapy system 100, the radiation treatment device 101, and the controller 116 can communicate with a network as well as databases and servers, for example, a dose calculation server (e.g., distributed dose calculation framework) and/or a treatment planning system 118 and/or a radiation treatment management system (RTMS) 119. The controller 116 may also be configured to transfer medical image related data between different pieces of medical equipment.

The system 100 can also include a plurality of modules containing programmed instructions (e.g., as part of controller 116, or as separate modules within system 100, or integrated into other components of system 100), which instructions cause system 100 to perform different functions related to adaptive radiation therapy or other radiation treatment, as discussed herein, when executed. For example, the system 100 can include a treatment plan module operable to generate the treatment plan for the patient 110 based on a plurality of data input to the system by the medical personnel, a patient positioning module operable to position and align the patient 110 with respect to a desired location, such as the isocenter of the gantry, for a particular radiation therapy treatment, an image acquiring module operable to instruct the radiation therapy system and/or the imaging device to acquire images of the patient 110 prior to the radiation therapy treatment (i.e., pre-treatment images used for treatment planning and patient positioning) and/or during the radiation therapy treatment (i.e., in-treatment images), and to instruct the radiation therapy system 100 and/or the imaging device 101 or other imaging devices or systems to acquire images of the patient 110.

The system 100 can further include a radiation dose prediction module operable to predict a dose to be delivered to the patient 110 before commencement of the radiation treatment therapy, a dose calculation module operable to calculate the actual dose delivered to the patient 110 during radiation therapy treatment, a treatment delivery module operable to instruct the radiation therapy device 100 to deliver the treatment plan to the patient 110, a correlation module operable to correlate the planning images with the in-treatment images obtained during radiation therapy, a computation module operable to reconstruct three-dimensional target volumes from in-treatment images, an analysis module operable to compute displacement measurements, and a feedback module operable to instruct the controller in real-time to stop radiation therapy based on a comparison of the calculated displacement with a predetermined threshold value (range).

The system 100 can further include one or more contour generation modules operable to generate contours of target volumes and other structures in pre-treatment (planning) and in-treatment (in-treatment session) images, an image registration module operable to register pre-treatment/planning images with subsequent in-treatment images, a dose calculation module operable to calculate accumulated dose, a contour propagation module operable to propagate a contour from one image to another, a contour verification module operable to verify a generated contour, a registration deformation vector field generation module operable to determine deformation vector fields (DVFs) as a result of an image deformation process. The modules can be written in the C or C++ programming language, for example. Computer program code for carrying out operations as described herein may be written in any programming language, for example, C or C++ programming language.

The treatment planning system 118 can be used to generate treatment plans for the radiation treatment device 101 based on image data, such as CT image data. In a typical planning process, qualified medical personnel manually draw contours on one or more of the initial planning images. These contours delineate the malignant tumor that is to be irradiated, as well as one or more other structures, such as organs, tissue, etc. that are susceptible to substantial damage from radiation exposure. The planning images can also be semi-automatically segmented to delineate the malignant tumor that is to be the target of the irradiation, and any surrounding critical structures whose irradiation should be limited. These images can also illustrate soft tissues, organs, blood vessels, bones, etc.

Additionally, or alternatively, the treatment planning system 118 can use information from other imaging modalities, such as MRI, PET, etc., and/or other image data for generating one or more treatment plans.

Figure 2:
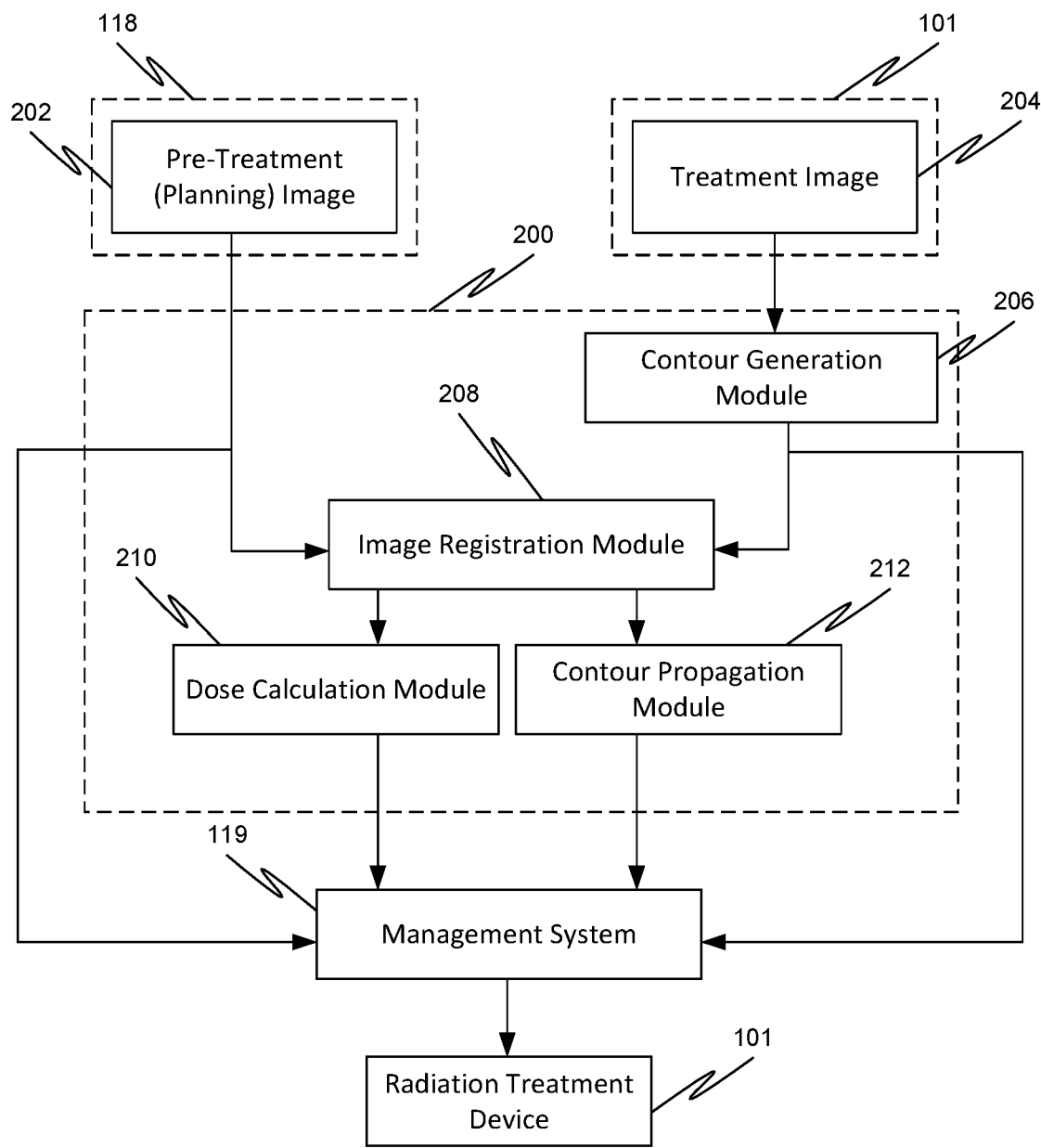
FIG. 2 is a process flow diagram for a method for automatically generating contours in a treatment image for use in adaptive radiation therapy, according to various embodiments of the disclosed subject matter.

FIG. 2 shows an exemplary flow of a method for automatically generating structures/contours in a treatment image 204 for use in adaptive radiation therapy, for example, by propagating the structures/contours from the planning image 202 onto the treatment image 204 using deformable registration.

First, a reference image 202 is obtained from the treatment planning system 118. The reference image 202 may be an image that was obtained previously, e.g., in a different imaging session, for the same or a different patient, that may have occurred on a different day, or on the same day. The reference image 202 may also be an image of a different individual, in which case, the image registration can be used to map the patient image to an atlas patient image. The reference image 202 may also be an image that was artificially created that does not correspond to any individual.

In an exemplary embodiment, the image 202 is a planning image obtained for the patient 110 during the treatment planning phase.

The planning image 202 contains one or more structures/contours that were generated during the planning phase. These contours delineate desired structures, such as one or more target volumes, one or more affected organs, and one or more anatomical structures of interest. For example, image 202 may contain a contour of a target volume including the primary tumor (i.e., primary target), the primarily affected organ (i.e., primary organ), and a region where invasion of lymph nodes has been observed or is to be expected (i.e., nodal target). Alternatively, image 202 may contain a contour of a target volume including the primary target, the primary organ, and the nodal target, and may contain one or more contours delineating other anatomical structures of interest. Alternatively, image 202 may include contours of a plurality of target volumes. Alternatively, image 202 may contain contours of a plurality of target volumes, with each target volume including a different type of primary and/or nodal target and/or primary organ. Alternatively, image 202 may include contours of a plurality of target volumes and one or more primary organs and one or more other anatomical structures of interest.

Planning image 202 also includes one or more contours of structures that influence one or more of the shape, size, and location of one or more of the primary target, the nodal target, the primary organ, and the anatomical structures of interest. These influencer structures include structures that generally move and/or deform significantly from day to day. The large movements and deformations of these structures can therefore influence the shape, size, and/or location of one or more of the other delineated structures. The contours of these influencer structures generally do not propagate well from the planning image 202 onto the treatment image 204 due to their highly deformable nature. These influencer structures may include, for example, organs, that exhibit large day to day deformations and/or movements.

Figure 4:
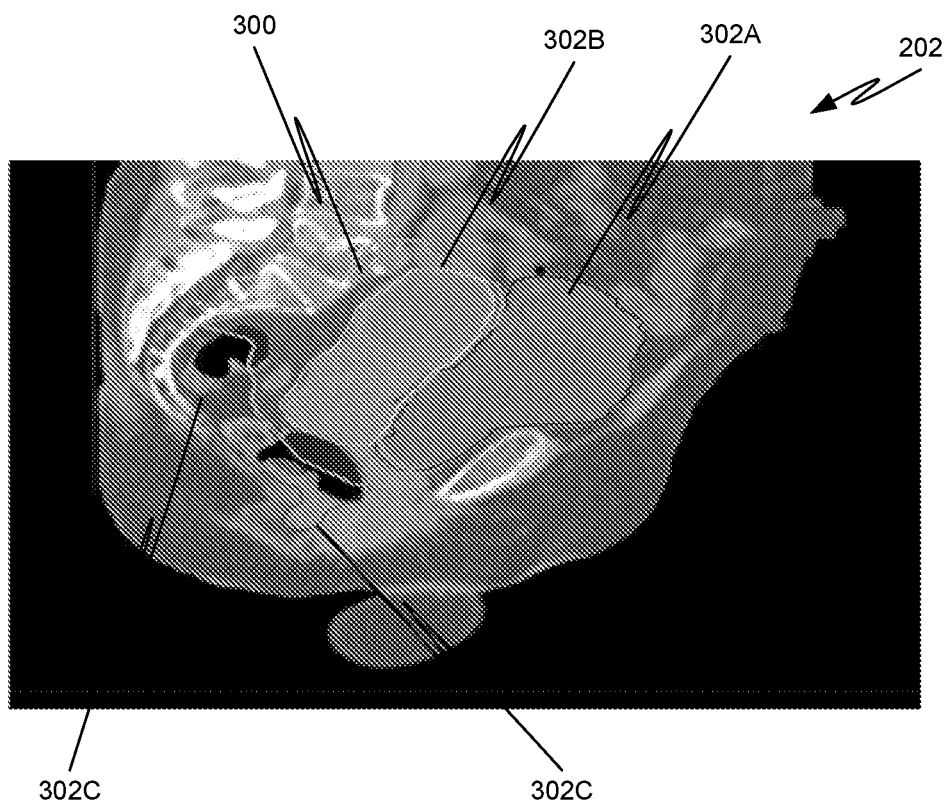
FIG. 4 is an exemplary sagittal CT slice showing a target volume and influencer structures in a female pelvis.

FIG. 4 shows an exemplary planning image 202 for a cervix uteri treatment. The planning image 202 includes a contour 300 delineating the primary and nodal targets as the target volume, and a set of influencer structure contours 302, such as a contour 302A delineating the bladder, a contour 302B delineating the uterus, and contours 302C delineating the rectum. Image 202 may also include other structures of interest, such as body outlines or femoral heads, etc., as shown in FIG. 4.

Figure 5A:
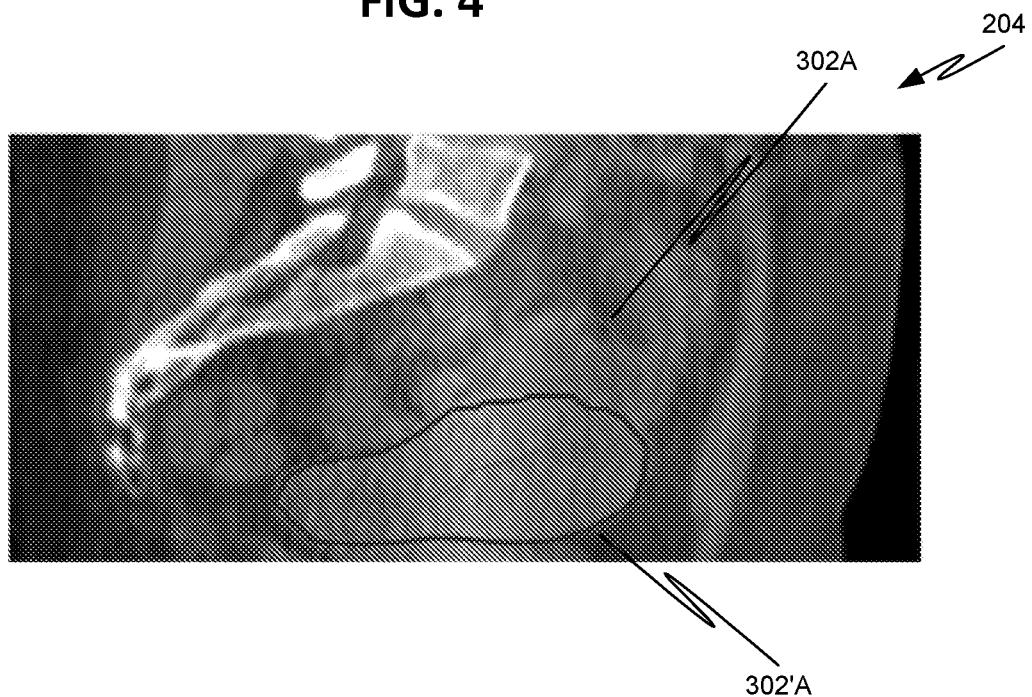
FIG. 5A is an exemplary sagittal CT slice showing a motion range of an influencer structure.
Figure 5B:
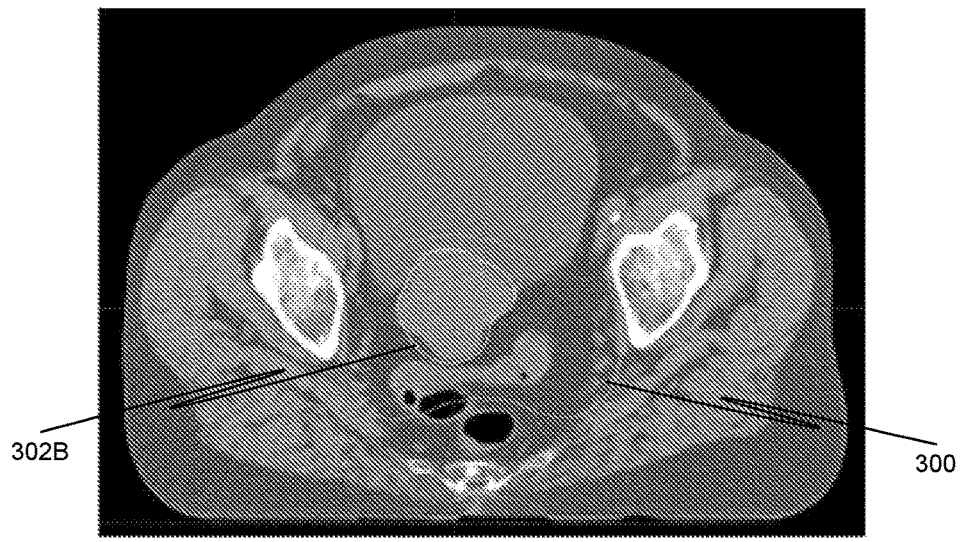
FIGS. 5B-5D are exemplary axial CT slices showing the motion range of a target volume and influencer structure.
Figure 5C:
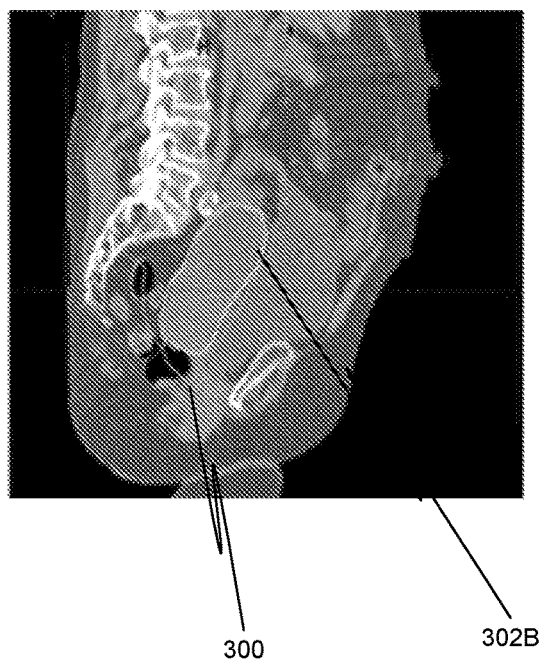
Figure 5D:
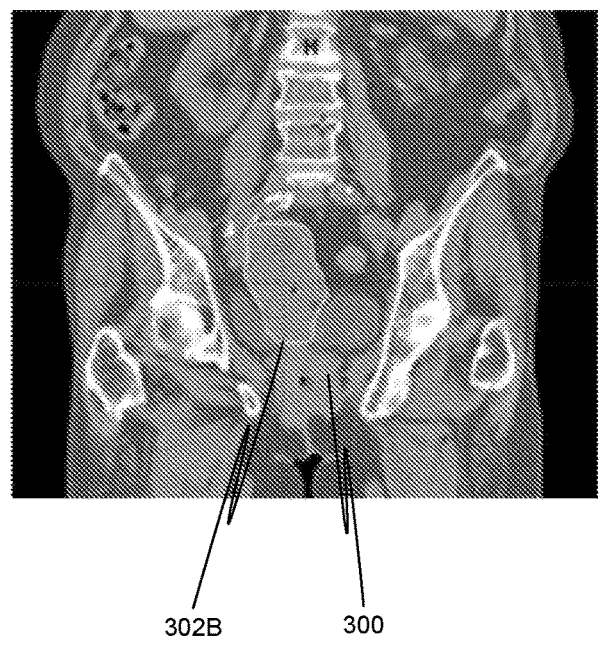

FIG. 5A shows the bladder 302A as an influencer structure that moves from day to day, and FIGS. 5B-5D show how a target volume 300A that moves from day to day due to the movement of the uterus 302B.

Although these images show specific structures used for the target volume and influencer structures, it is to be understood that the target volumes and influencer structures are not limited to these specific structures, and that any structures may be used that are relevant for a specific treatment, such as, but not limited to, the treatment of prostate, pancreas, rectal cancer, etc.

For ease of illustration, the structures in the planning image 202 that are not influencer structures are illustrated as a first set of structures 300, and the structures that are influencer structures are illustrated as a second set of structures 302. The first set of structures 300 can include one or more of a primary target, a nodal target, a primary organ, and any other anatomical structures of interest. The second set of structures 302 can include one or more of structures, such as organs for example, that influence one or more of the structures in the first set of structures 300 (see FIG. 3).

Next, a treatment image 204 of the portion of the patient 110 that is of interest is acquired using the radiation treatment device 101. In an exemplary embodiment, the image 204 is a CT image obtained during a treatment session by irradiating the region of interest of the patient 110 with radiation 120. This image does not include any delineations.

Prior to initiating image registration between the planning image 202 and the treatment image 204 by the image registration module 208, the contour generation module 206 can initiate a contour generation process on treatment image 204 to delineate the same set of influencer structures that were delineated in the planning image 202.

Figure 3:
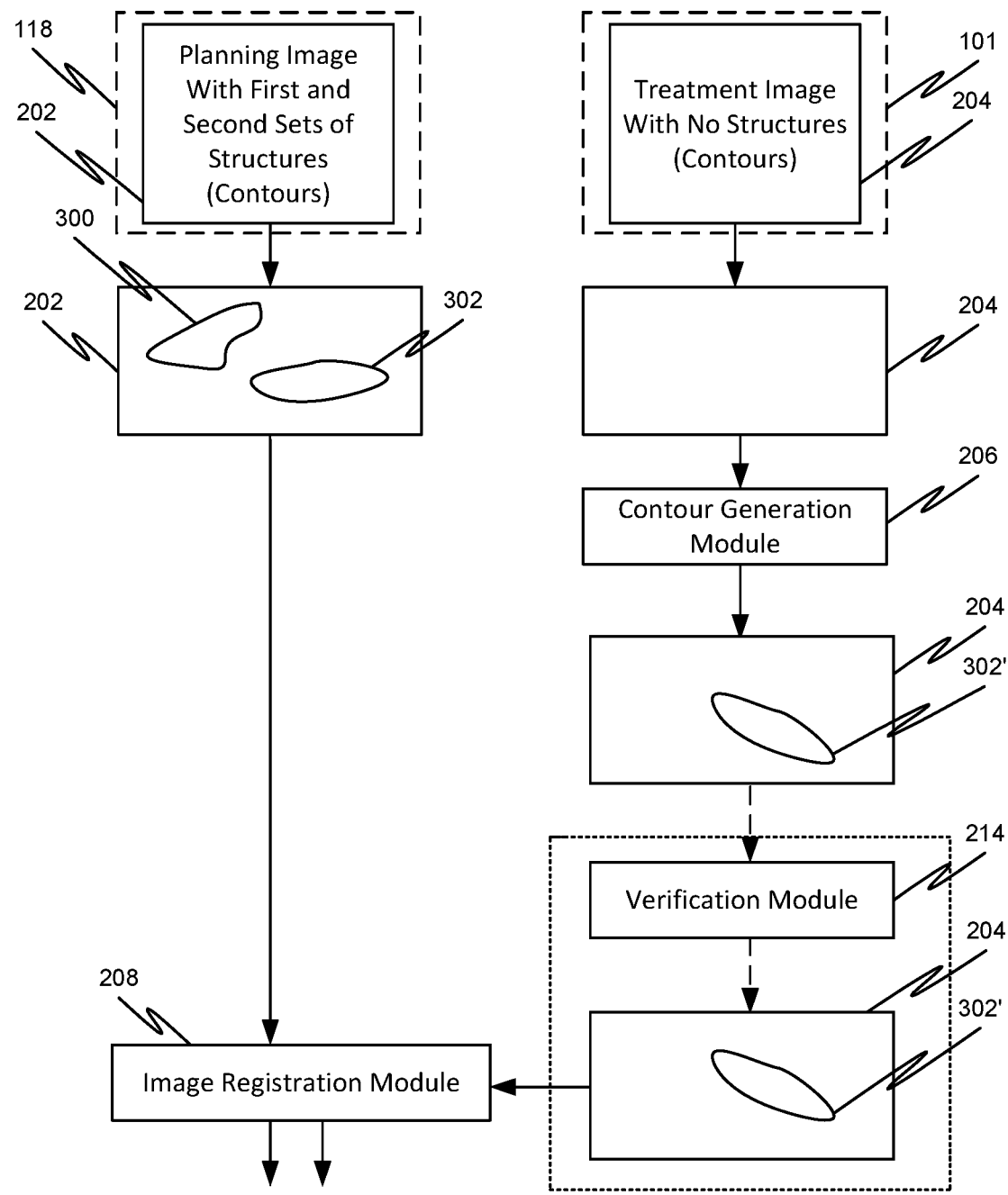
FIG. 3 is a process flow diagram for obtaining a planning image and a treatment session image, according to various embodiments of the disclosed subject matter.

As shown in FIG. 3, when initiated, the influencer structures are automatically delineated using various available automatic segmentation algorithms, that automatically detect and draw the contours. The delineation can also be done manually by medical personnel via an interactive graphical interface (GUI) for example, that allows the medical personnel to identify and draw the contours 302' on the treatment image 204.

Figure 6:
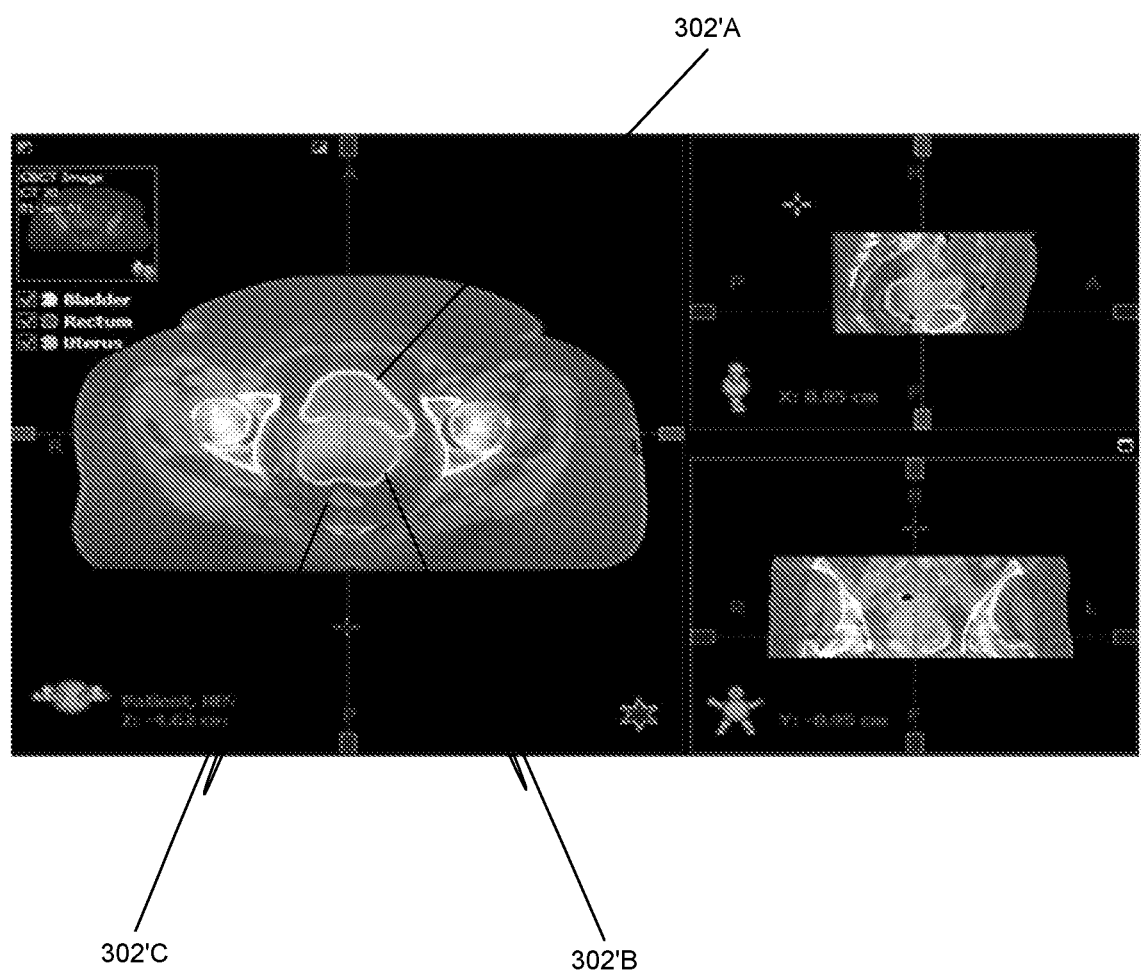
FIG. 6 illustrates a screen shot of an exemplary contour verification process display.

Once the contours 302' of the influencer structures 302 are drawn on the treatment image 204, the contours 302' may be further reviewed by the medical personnel using various available contour verification tools present in the verification module 214 of the GUI, for example. Using the GUI, the medical personnel can modify, delete, redraw the automatically generated contours 302', to establish consistency between the influencer structures 302 in the planning image 202 and the influencer structures 302 in the treatment image 204. An exemplary verification process is shown in FIG. 6, where the contours for the bladder 302'A, the uterus 302'B, and the rectum 302'C are reviewed from different views on a display device of a GUI.

Since the influencer structures 302 deform significantly, the location of the influencer structures 302 on the treatment image 204 may be different from the location of the same influencer structures 302 in the planning image 202, as shown in FIGS. 5A-5D.

Next, the image registration module 208 initiates image registration between the planning image 202 that contains the first set of structures 300 and the second set of structures 302 (i.e., the influencer structures), and the treatment image 204 that contains the second set of structures 302' (i.e., influencer structures) located at a different location than in the planning image 202. The image registration can be a deformable registration which registers the image data of the planning image 202 with the image data of the treatment image 204 using a deformable registration algorithm, and which generates, as a result, one or more deformable vector fields (DVFs) 222 (see FIG. 7) that can be used to propagate the first set of structures 300 from the planning image 202 to the treatment image 204 using the contour propagation module 212. The one or more deformable vector fields (DVFs) 222 can also be used for dose accumulation determination by the dose calculation module 210.

The management system 119, which could be a stand-alone system or could be integrated with the controller 116 and/or the input/output device 117, can initiate the contouring of the propagated first set of structures (i.e., 300'' in FIG. 8) based on the propagated image data (i.e., 300' in FIG. 8), and/or to manage the treatment image 204 that includes the propagated first set of structures 300'' and the second set of structures 302', and to manage the calculated dose accumulation for further radiation processes involved in adaptive radiation treatment or any other radiation treatment processes. For example, the treatment image 204 including the propagated first set of structures 300'' and the second set of structures 302' can be used to identify the differences between the planning image 202 and the treatment image 204 and/or one or more subsequent images, and to generate a new treatment plan based on the obtained differences.

Alternatively, the controller 116 can fully manage the processes of the management system 119, and therefore the management system 119 is either not needed or works together with the controller 116 and/or the input/output device 117 to accomplish the managing.

Figure 7:
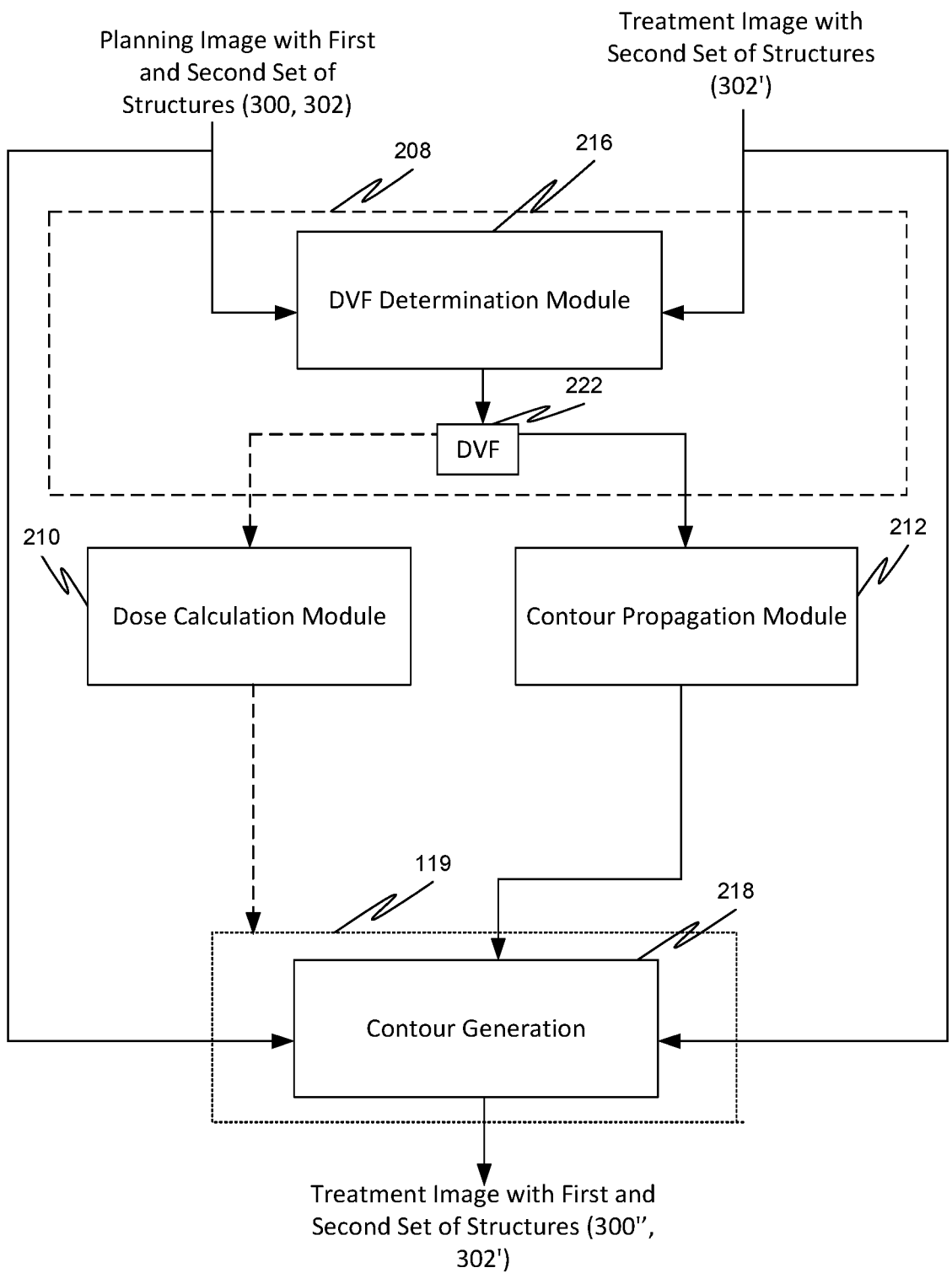
FIG. 7 is a process flow diagram for contour generation, according to various embodiments of the disclosed subject matter.

FIG. 7 illustrates an exemplary deformable image registration process used to automatically generate structures in a treatment image 204 to be used for adaptive therapy, for example. The generated structures, namely, the contour 300'' of the propagated first set of structures 300 and the contour 302' of the second set of structures 302 are anatomically consistent with the initially defined contours of structures 300 and 302 in the planning image 202 but adapted to the locations of the anatomies at the time of radiation delivery.

First, the planning image 202, which includes the first set of structures 300 and the second set of structures 302, is compared and spatially registered with the treatment image 204, which includes the second set of structures 302', using a structure-guided deformable registration algorithm 220 (see FIG. 8) used in the deformable registration process. The deformable registration quantifies the differences between the image data of the planning image 202 and the image data of the treatment image 204 and minimizes them. As a result, a plurality of vectors is generated using a DVF determination module 216 that map voxels of each prescribed location in the planning image 202 to a location in the treatment image 204, giving for each point the vector from that point in the planning image 202 to the point to which it corresponds in the treatment image 204. Each of the plurality of vectors corresponds to a control point, and each vector has a direction that represents a direction in which a control point in the planning image 202 moves to reach the location as the control point appears in the treatment image 204. Each vector also has a magnitude that represents a distance that a control point in the planning image 202 travels in the corresponding direction to reach the location as the control point appears in the treatment image 204. The so obtained plurality of individual vectors aggregated into one or more maps are the deformation vector fields (DVFs) 222. The one or more deformation vector fields (DVFs) 222 specify the coordinate transformation between the two datasets.

The one or more deformation vector fields (DVFs) 222 can be applied by the contour propagation module 212 to propagate the first set of structures 300 from the planning image 202 to the treatment image 204. The one or more deformation vector fields (DVFs) 222 can also be used to calculate dose accumulation by the dose calculation module 210. The contour 300'' of the propagated first set of structures 300 can be drawn by a contour generation module 218 using a contour drawing tool, for example.

Figure 8:
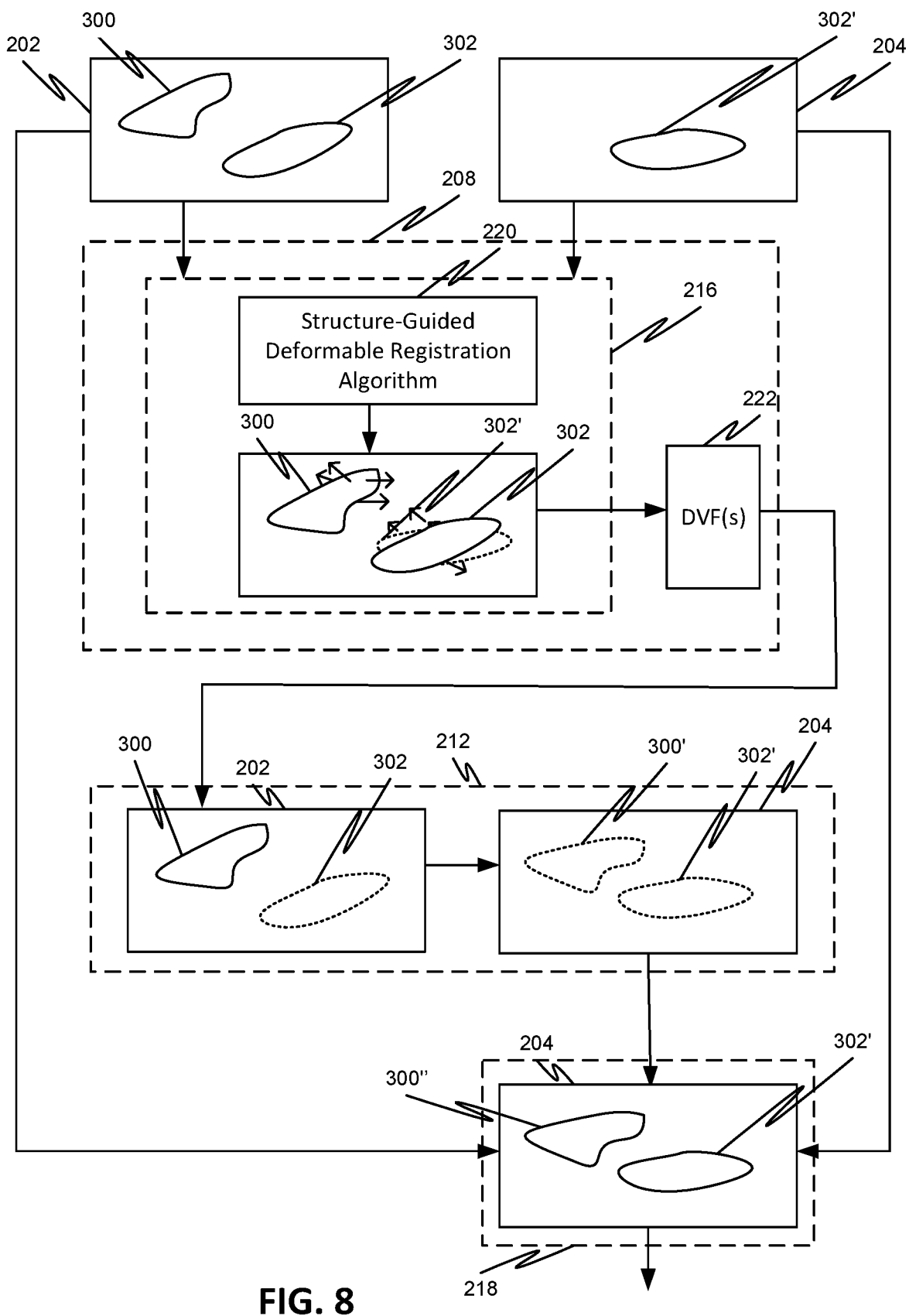
FIG. 8 is a process flow diagram for contour generation using structure guided deformable registration, according to various embodiments of the disclosed subject matter.

FIG. 8 illustrates an exemplary propagation process. As shown in FIG. 8, prior to the generation of the contour 300'', the generated one or more deformation vector fields (DVFs) 222 are applied on the planning image 202 to align the first set of structures 300 in the planning image 202 on the treatment image 204. The image data 300' so obtained represents the image data of the first set of structures 300 propagated to the treatment image 204. The contour 300" of the first set of structures 300 is drawn in the treatment image 204 based on the image data 300' using a contour drawing tool, for example. Thus, the deformation vector fields (DVFs) 222 facilitate the transfer of information that allows the medical personnel to perform the contouring.

The treatment image 204 now includes the newly generated first set of structures 300" as well as the second set of structures 302' which are anatomically consistent with the initially defined structures 300 and 302 in the first image but adapted to the locations of the anatomies at the time of radiation delivery. This treatment image 204 can then be used for adaptive radiation therapy, for example. The treatment image 204 can also be used for any other radiation treatment process.

In order to propagate the first set of structures 300 from the planning image 202 to the treatment image 204, control points on the first set of structures 300 need to be matched with corresponding points in the second image 204 using a deformable registration algorithm that determines the gray level intensity of each voxel in the planning image 202 and the treatment image 204, and determines a gradient that indicates the directional change in the intensity in the immediate neighborhood of the voxel. Commercially available deformable registration algorithms such as, but not limited to, the Demons deformable registration or the B-spline technique, for example, do not generate an acceptable deformation vector field (DVF) 222 due, in part, to the fact that these deformable registration algorithms do not account for the different deformation properties of the structures within the target volume, nor do they account for the strong deformations of structures.

Figure 9A:
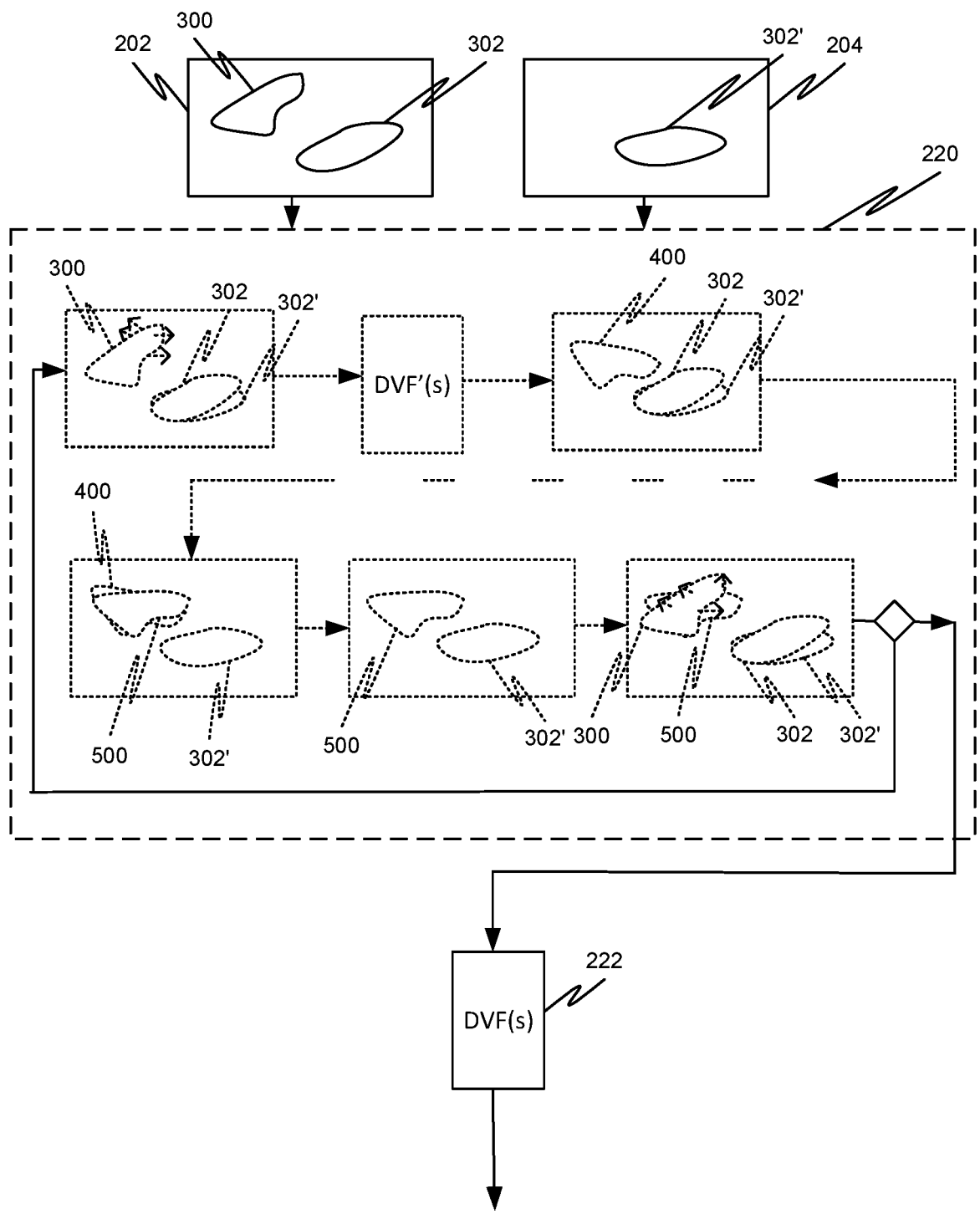
FIGS. 9A-9B are process flow diagrams illustrating aspects of using influencer structures to guide the deformable registration process, according to various embodiments of the disclosed subject matter.

FIG. 9A illustrates an exemplary process to obtain the one or more deformable registration fields (DVFs) 222 by the deformable registration module 216 using a structure-guided deformable registration algorithm 220. The structure-guided deformable registration algorithm is a deformable registration algorithm that is adapted to use the set of influencer structures 302, 302' as guides to thereby obtain deformation vector fields (DVFs) 222 that accurately propagate the first set of structures 300 from the planning image 202 to the treatment image 204.

Additionally, or alternatively, the structure-guided deformable registration algorithm 220 is also adapted to consider the different deformation properties of different structures.

In order to obtain the one or more deformation vector fields (DVFs) 222, the structure-guided deformable registration algorithm 220 starts with the image data of the planning image 202 and the image data of the treatment image 204 as an initial input, and proceeds with the computation through a plurality of steps in order to determine the one or more deformation vector fields (DVFs) 222 that optimize the similarity measures between the planning image 202 and the treatment image 204 (i.e., the measure of how well the planning image 202 matches with treatment image 204).

As a first step in the computation, the planning image 202, which includes the first set of structures 300 and the second set of structures 302, is compared and spatially registered with the treatment image 204, which includes the second set of structures 302'. As a result, a plurality of vectors is generated that map voxels of each prescribed location in the planning image 202 to some location in the treatment image 204, giving for each point the vector from that point in the planning image 202 to the point to which it corresponds in the treatment image 204. Each of the plurality of vectors corresponds to a control point, and each vector has a direction that represents a direction in which a control point in the planning image 202 moves to reach the location as the control point appears in the treatment image 204. Each vector also has a magnitude that represents a distance that a control point in the planning image 202 travels in corresponding direction to reach the location as the control point appears in the treatment image 204. The so obtained plurality of individual vectors aggregated into one or more maps are the deformation vector fields (DVFs').

The generated deformation vector fields (DVFs') can then be applied on the planning image 202 to align the first set of structures 300 in the planning image 202 onto the treatment image 204, and thereby obtain the propagated image data 400.

The one or more deformation vector fields (DVF's) can be constrained to match points in the second set of structures 302 in the planning image 202 (i.e., points within contour 302) with points in the second set of structures 302' in the treatment image 204 (i.e., points within contour 302'). This matching aligns the second set of structures 302 in the planning image 202 with the second set of structures 302' in the treatment image 204 and modifies the propagated image data 400 to image data 500. The constraining of the one or more deformation vector fields (DVF's) can be done by implementing a constraint in the structure-guided deformable registration algorithm to force intensity matching between the second set of structures 302 in the planning image 202 and the second set of structures 302' in the treatment image 204, which then forces the second set of structures 302 in the planning image 202 to match the second set of structures 302' in the treatment image 204.

The image data of the planning image 202 can then be mapped to the image data of the treatment image 204 containing modified image data 500. As a result of the mapping, one or more deformation vector fields (DVFs) 222 are generated. Since the image data 500 is obtained due to the matching of the second set of structures 302 in the planning image 202 with the second set of structures 302' in the treatment image 204, the obtained one or more deformable vector fields (DVFs) 222 are in effect guided by the second set of structures 302, 302'.

The above enumerated steps are exemplary only, and it is to be understood that the algorithm may go through multiple similar iterations before obtaining the optimal one or more deformation vector fields (DVFs) 222 that are used for the propagation, and/or may go through fewer iterations, and/or may include only some of the iterations.

Figure 9B:
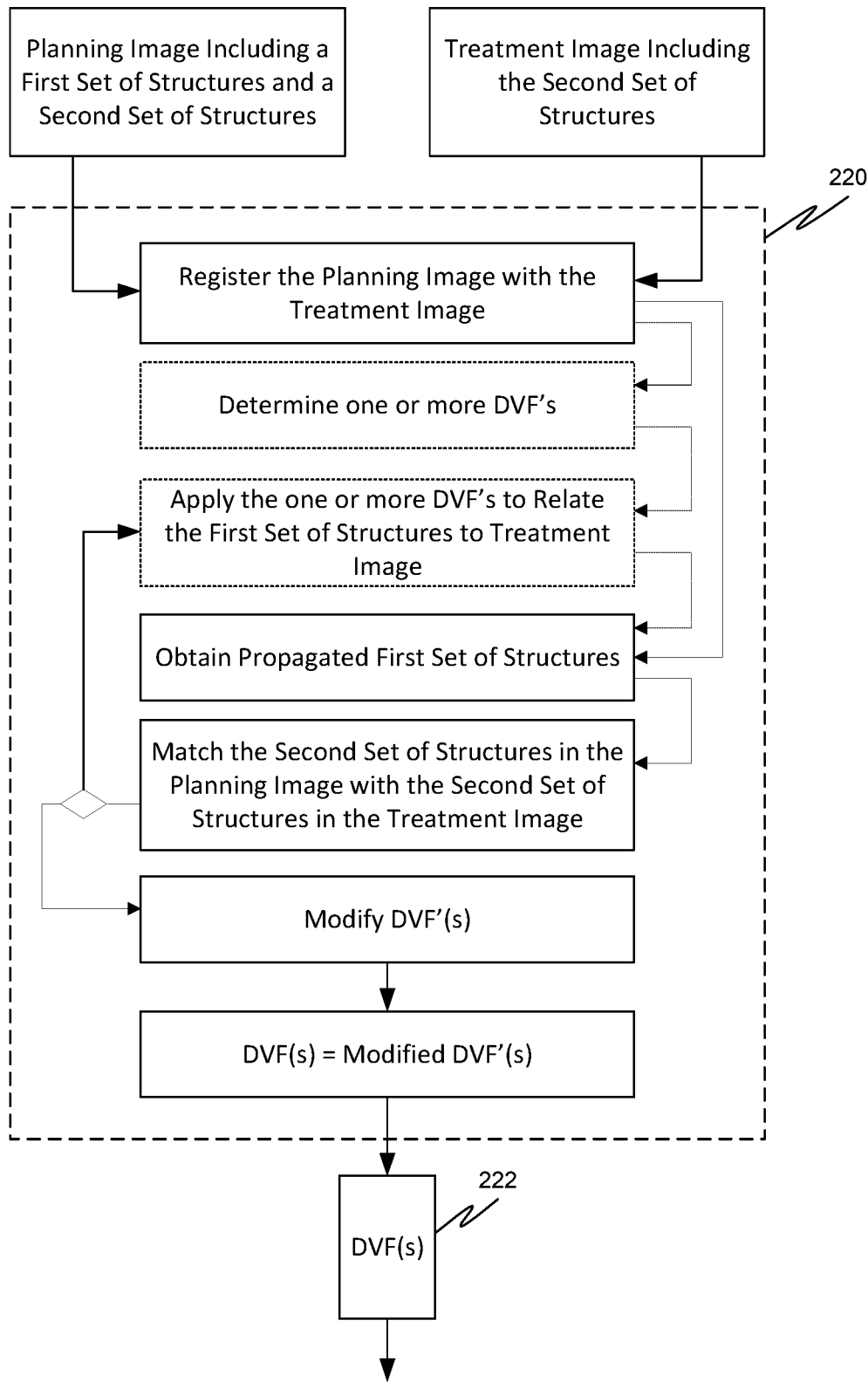

For example, the structure-guided deformable registration algorithm 220 enables the generating of the one or more deformable vector fields (DVFs) 222 through process steps as illustrated in FIG. 9B. In a first step, the planning image 202 containing the first set of structures 300 and the second set of structures 302 is registered with the treatment image 204 containing the second set of structures 302'. As a result, propagated image data 400 for the first set of structures 300 is obtained. Optionally, the structure-guided deformable registration algorithm 202 may include a step of obtaining, as result of registering, one or more deformable vector fields DVF's, which when applied on the planning image 202 to relate the first set of structures 300 to the treatment image 204, generate the propagated image data 400 for the first set of structures 300. By constraining the structure-guided deformable registration algorithm to force the second set of structures 302 in the planning image 202 to match the second set of structures 302' in the treatment image 204, namely, forcing the contours 302 and 302' to match, the propagated image data for the first set of structures is correspondingly modified based on the matching. The one or more deformable vector fields (DVFs) 222 are then obtained based on the modified propagated image data.

Additionally, the deformable registration may be further improved to take into consideration the varying deformation properties of different structures. For example, points in the nodal regions that are located close to the bone or around blood vessels, which practically do not move independently of the bones and/or the blood vessels, can be considered to be points which deform rigidly, and points in the nodal regions that are not located close to the bones or around blood vessels can be considered to be points which deform non-rigidly (rigid deformations assume that the structure to be propagated may have shifted or rotated, but not changed shape and/or size, whereas non-rigid deformations take into consideration shape and/or size changes). By assigning constraints to the transformation to force certain points in a structure to deform rigidly and other points in the structure to deform non-rigidly, the deformable registration enables accurate propagation of structures that have different deformations properties.

Figure 13A:
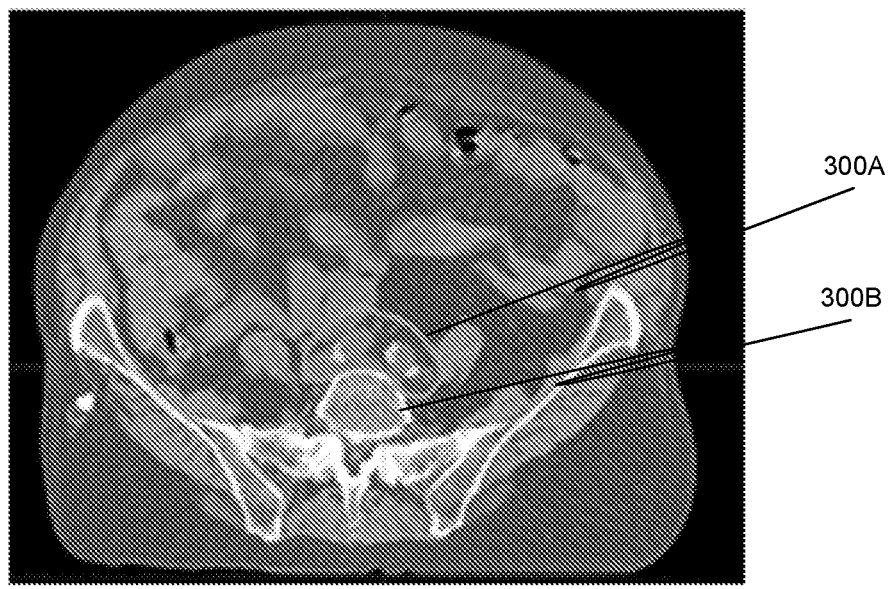
FIGS. 13A-13B illustrate target volumes with portions that deform differently, according to various embodiments of the disclosed subject matter.
Figure 13B:
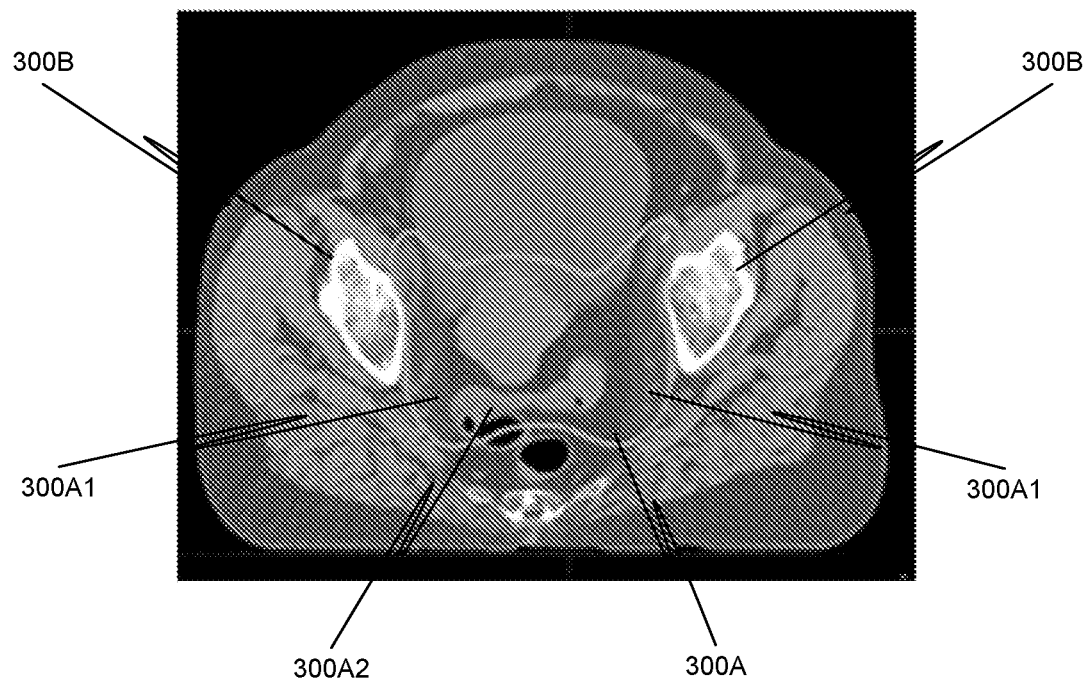

In an exemplary embodiment shown in FIGS. 13A and 13B, a first set of structures 300 includes a first structure 300A and a second structure 300B, which is a bone. The first structure 300A is located near the second structure 300B, such that portions 300A1 of the first structure are located close to the bone 300B and a portion 300A2 which is not located close to the bone. Since the portions 300A1 of the first structure 300A are located close to the bone, these portions 300A1 do not move independently of the bone 300B, whereas portion 300A2 moves independently of the bone 300B. Portions 300A1 therefore could be considered to deform rigidly as the bone 300B does, whereas portion 300A2 could be considered to deform non-rigidly. By assigning constraints to the deformation vector field (DVF) 222 to force points located in portions 300A1 to deform rigidly and points located in portions 300A2 to deform non-rigidly, the resulting contour 300" that was propagated onto image 204 accurately reflects the different deformations properties of structure 300A.

Figure 10:
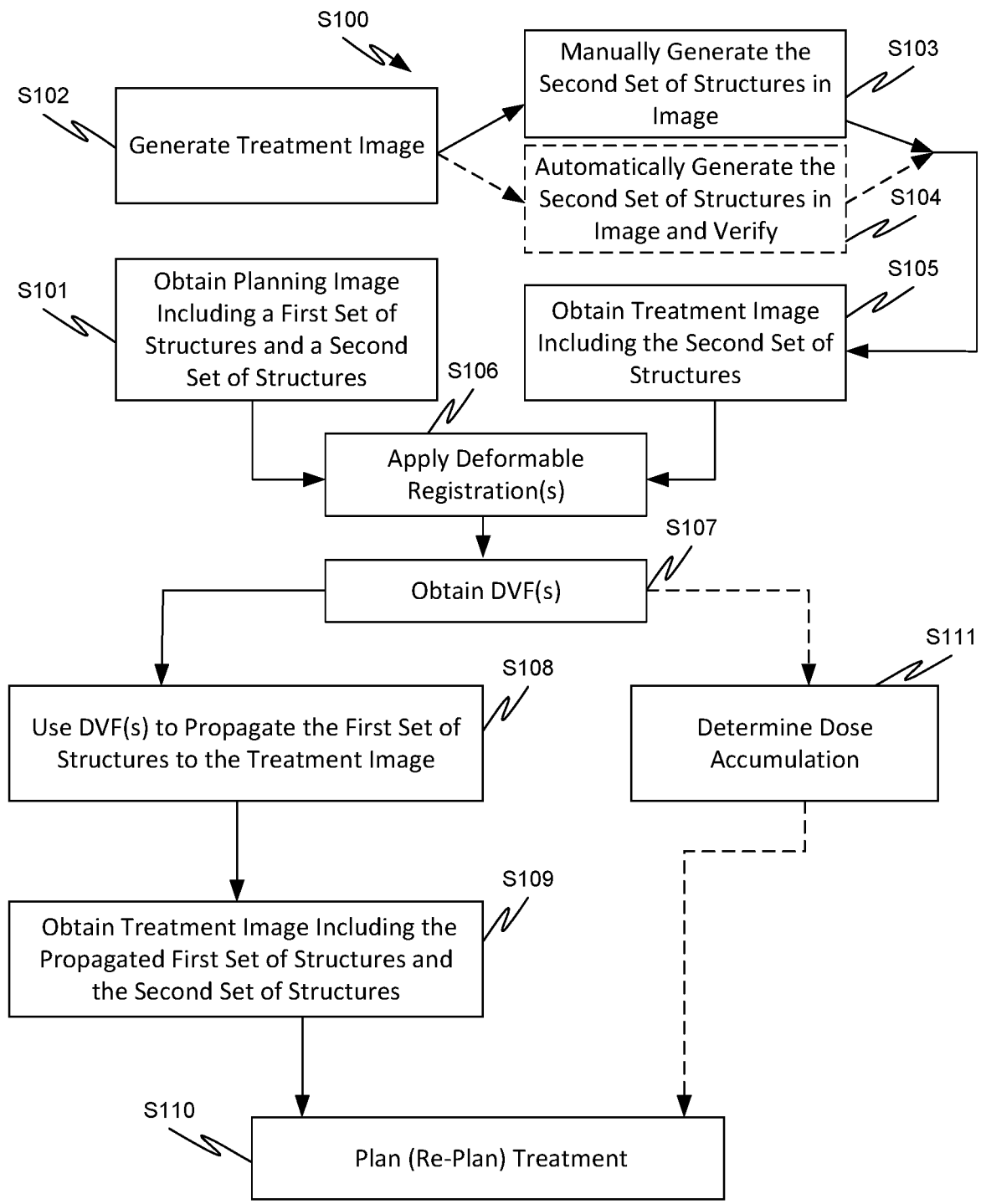
FIG. 10 is a process flow diagram illustrating aspects of a structure-guided deformable registration process to automatically generate structures used in adaptive radiotherapy, according to various embodiments of the disclosed subject matter.

FIG. 10 illustrates a flow chart of a method S100 for automatically generating one or more structures in a treatment image 204 using one or more deformation vector fields (DVFs) 222. Generally, once the planning image 202 and the treatment image 204 are obtained, the image data from the planning image 202 and the treatment image 204 are used as inputs in the deformable registration process to obtain one or more deformation vector fields (DVFs) 222, which are then used to propagate the one or more structures from the planning image 202 to the treatment image. The treatment image 204 that contains all the structures of the planning image 202 after propagation can then be used to determine whether re-planning or further planning is necessary.

In an exemplary embodiment, a single deformation vector field (DVF) 222 is generated and used to propagate the first set of structures (i.e., contours, for example) 300 onto the treatment image 204.

In step S101, a planning image 202 is obtained by the controller 116 from the TPS 118. The planning image 202 may be a CT image that includes one or more contours of a first set of structures 300 and one or more contours of a second set of structures 302. In an exemplary embodiment, the first set of structures 300 includes a contour of a target volume including a primary target and a nodal target as well as a contour of an organ of interest, and the second set of structures 302 (i.e., influencer structures) includes contours of one or more organs, other than the primary organ included in the target volume, that influence one of a shape, size, and location of the primary target. Planning image 202 may also include other anatomical structures of interest in the first set of structures 300.

In step S102, a treatment image 204 is generated in the radiation treatment device 101 of the same portion of the patient 110. The treatment image 204 may be an in-treatment CT image that does not include any delineations of the target volume.

In step S103, a medical specialist can manually draw contours on the image 204 to delineate the same influencer structures 302 found in the planning image 202 on treatment image 204 (i.e., influencer structures 302'). The delineated influencer structures 302' on treatment image 204 are most likely in different locations than the same influencer structures 302 are in planning image 202.

Alternatively, in step S104, the influencer structures 302' can be automatically detected in treatment image 204 and delineated using various contouring tools. The automatically generated contours 302' are also verified for consistency by the specialist.

Alternatively, the influencer structures 302' can be delineated using a combination of manual and automatic contouring.

In step S105, the controller 116 also obtains the treatment image 204 that now includes the contour 302' of the same set of influencer structures that were delineated in the planning image 202.

In step S106, the two images 202 and 204 are exposed to a deformable registration process by which a structure-guided deformable registration algorithm is applied to deformably register the two images and thereby generate a deformation vector field (DVF) 222 in step S107.

Next, in step S108, the deformation vector field (DVF) 222 is used to propagate the first set of structures 300 from the planning image 202 to the treatment image 204. The propagation results in a propagated image data 500 for the first set of structures 300, which then is used in step S109 to obtain the contour 300" of the first set of structures 300 on the treatment image 204. The resulting treatment image 204 contains the first set of structures 300" as well as the second set of structures 302', which are anatomically consistent with the initially defined structures 300 and 302 in the planning image 202 but adapted to the locations of the anatomies at the time of the fraction delivery.

The treatment image 204 can then be used for adaptive radiation therapy in step S110 to re-plan the treatment according to the discrepancies between the planning image 202 and the treatment image 204.

Alternatively, or additionally, the treatment image 204 can be used in any other radiation treatment system or process.

The deformation vector field (DVF) 222 obtained in step S107 can also be used to determine dose accumulation in Step S111. In an exemplary embodiment, the deformation vector field (DVF) 222 can be used to accumulate the doses for multiple delivered fractions. The doses can be added based upon location of the doses in physical space, or upon doses based upon the structures that receive the dose, even if the structures have changed location.

Figure 11:
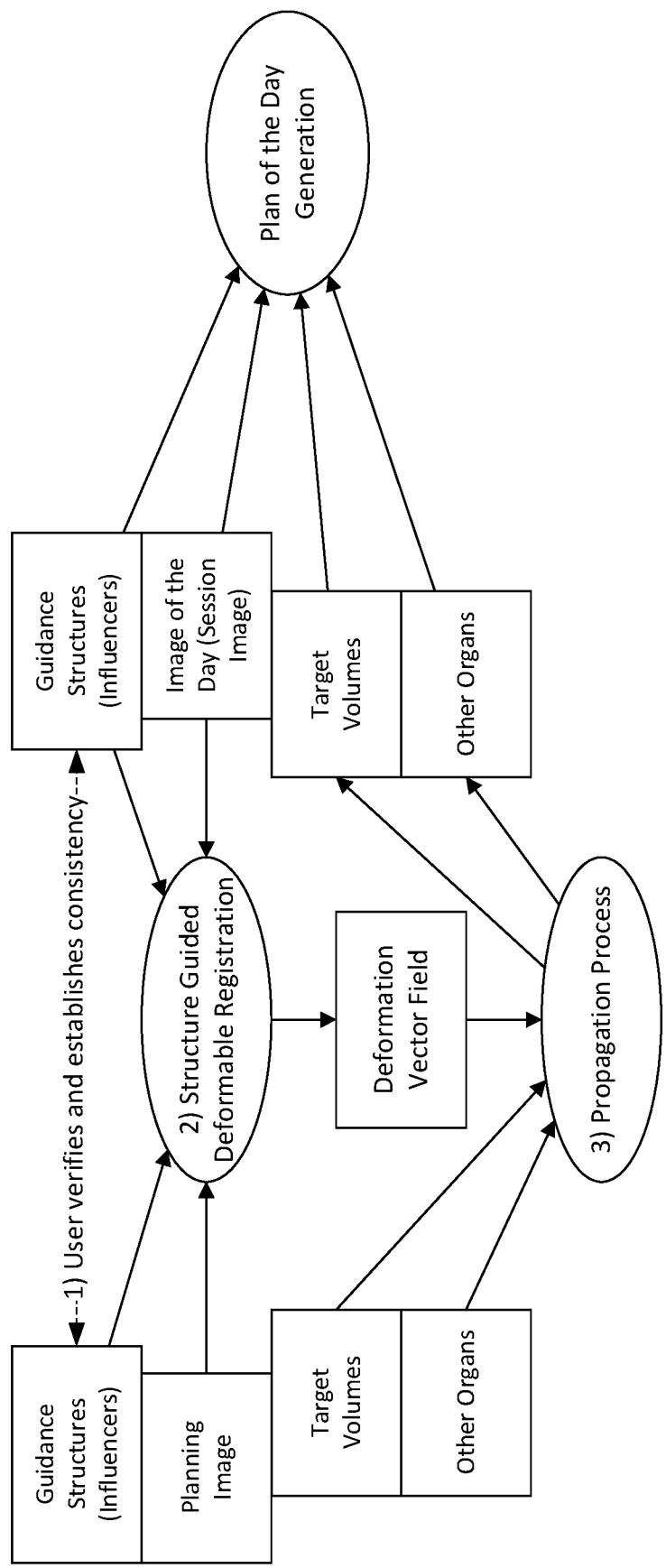
FIG. 11 illustrates an exemplary process using a single deformation vector field to propagate target volumes, according to various embodiments of the disclosed subject matter.

The exemplary process S100 can be applied to a planning image 202 as shown in FIG. 11, for example, where the planning image includes a target volume and one or more organs, as well as the guiding structures (i.e., influencers), and a subsequently acquired image, which can be an image acquired during a treatment session (i.e., image of the day), for example. The image of the day also includes the same guiding structures as the planning image. After verifying that the guidance structures in the two images match, a structure-guided deformable registration algorithm is applied to deformably register the two images and thereby generate a deformation vector field (DVF) that is used to propagate the target volume and the one or more organs in the planning image onto the image of the day.

The image of the day, which now includes the contours of all structures, namely, the target volume, the one or more organs, and the guidance structures, is then used to generate the plan of the day, which could be different from the plan that was initially planned to be delivered onto the patient 110.

In another exemplary embodiment, different deformation vector fields (DVFs) 222 are generated and used to propagate different structures in the first set of structures (i.e., contours) 300 onto the treatment image 204. Each deformation vector field (DVF) 222 can be associated with a corresponding structure in the first set of structures 300. However, any combination of deformation vector fields (DVFs) 222 and structures can be applied. For example, a deformation vector field (DVF) 222 can be associated with one or a plurality of structures in the first set of structures 300.

In step S101, a planning image 202 is obtained by the controller 116 from the TPS 118. The planning image 204 may be a CT image that includes contours of a first set of structures 300 and one or more contours of a second set of structures 302. In an exemplary embodiment, the first set of structures 300 includes contours of a first target volume (target volume type 1), a second target volume (target volume type 2), as well as contours of one or more primary organs, and the second set of structures 302 includes contours of one or more organs, other than the primary organs included in the first set of structures 300, that influence one of a shape, size, and location of one or more structures in the first and second target volumes. The first target volume may include a primary target and a nodal target of a first type and the second target volume may include a primary target and a nodal target of a second, different type than the first target volume. Image 202 may also include other anatomical structures of interest in the first set of structures 300.

In step S102, an image 204 is generated in the radiation treatment device 101 of the same portion of the patient 110. The treatment image 204 may be an in-treatment CT image that does not include any delineations of the target volume.

In step S103, a medical personnel (specialist) can manually draw contours on the image 204 to delineate the same influencer structures 302 found in the planning image 202 on treatment image 204 (i.e., influencer structures 302'). The delineated influencer structures 302' on treatment image 204 are most likely in different locations than the same influencer structures 302 are in the planning image 202.

Alternatively, in step S104, the influencer structures 302' can be automatically detected in treatment image 204 and delineated using various contouring tools. The automatically generated contours 302' are also verified for consistency by the specialist.

Alternatively, the influencer structures 302' can be delineated using a combination of manual and automatic contouring.

In step S105, the controller 116 also obtains the treatment image 204 that now includes the contour 302' of the same set of influencer structures 302 that were delineated in the planning image 202.

In step S106, the two images 202 and 204 are exposed to one or more deformable registration processes to generate the different deformation vector fields (DVFs) 222 in step S107.

In an embodiment, a first deformation registration process is applied to the planning image 202 and the treatment image 204 to generate a plurality of vectors that map points on the contour of the first target volume (target volume type 1) and the one or more contours of the influencer structures 302 in the planning image 202 to locations in the treatment image 204, giving for each point, the vector from that point in the planning image 202 to the point to which it corresponds in the treatment image 204. The plurality of individual vectors so obtained are aggregated into a first map which is the first deformation vector field (DVF).

A second deformation registration process is applied to the planning image 202 and the treatment image 204 to generate a plurality of vectors that map points on the contour of the second target volume (target volume type 2) and the one or more contours of the influencer structures 302 in the planning image 202 to some locations in the treatment image 204, giving for each point, the vector from that point in the planning image 202 to the point to which it corresponds in the treatment image 204. The plurality of individual vectors so obtained are aggregated into a second map which is the second deformation vector field (DVF).

The first and second deformation vector fields (DVFs) are then applied on the planning image 202 to generate corresponding image data for the propagated contours of the first and second target volumes on treatment image 204 in step S108.

The resulting treatment image 204 contains the propagated contours as well as the second set of structures, which are anatomically consistent with the initially defined contours in the planning image 202 but adapted to the locations of the anatomies at the time of the fraction delivery.

The treatment image 204 can then be used for adaptive radiation therapy in step S110 to re-plan the treatment according to the discrepancies between the planning image 202 and the treatment image 204.

Alternatively, or additionally, the treatment image 204 can be used in any other radiation treatment system or process.

Alternatively, the plurality of deformation vector fields (DVFs) 222 can be aggregated into different sets of deformation vector fields (DVFs).

In an embodiment, a single deformable registration algorithm can be used to generate the plurality of deformation vector fields (DVFs) 222.

Alternatively, a plurality of different deformable registration algorithms can be used to generate the plurality of deformation vector fields (DVFs) 222.

In an exemplary embodiment, at least one of the deformable registration algorithms is a structure-guided deformable registration algorithm. In such an embodiment, the structure-guided deformable registration algorithm is applied to deformably register the two images 202, 204 and thereby generate at least one of the different deformation vector fields (DVFs) 222 that are used to propagate at least one of the target volumes in the first set of structures 300 from the planning image 202 to the treatment image 204. The deformable registrations that can be used in combination with the at least one structure-guided deformable registration can include, but are not limited to, Demons deformable registration or the B-spline technique, for example. Any other applicable deformable registration techniques can also be used.

By generating different deformation vector fields (DVFs) 222 for different target volumes, the accuracy of propagated target volumes is increased.

The treatment image 204 can then be used for adaptive radiation therapy in step S110 to determine whether to re-plan the treatment according to the discrepancies between the planning image 202 and the treatment image 204.

Alternatively, the treatment image 204 can be used for any other radiation treatment process.

The deformation vector fields (DVFs) 222 obtained can also be used to determine dose accumulation in step S111. In an exemplary embodiment, the deformation vector fields (DVFs) 222 can be used to accumulate the doses for multiple delivered fractions. The doses can be added based upon location of the doses in physical space, or upon doses based upon the structures that receive the dose, even if the structures have changed location.

Figure 12:
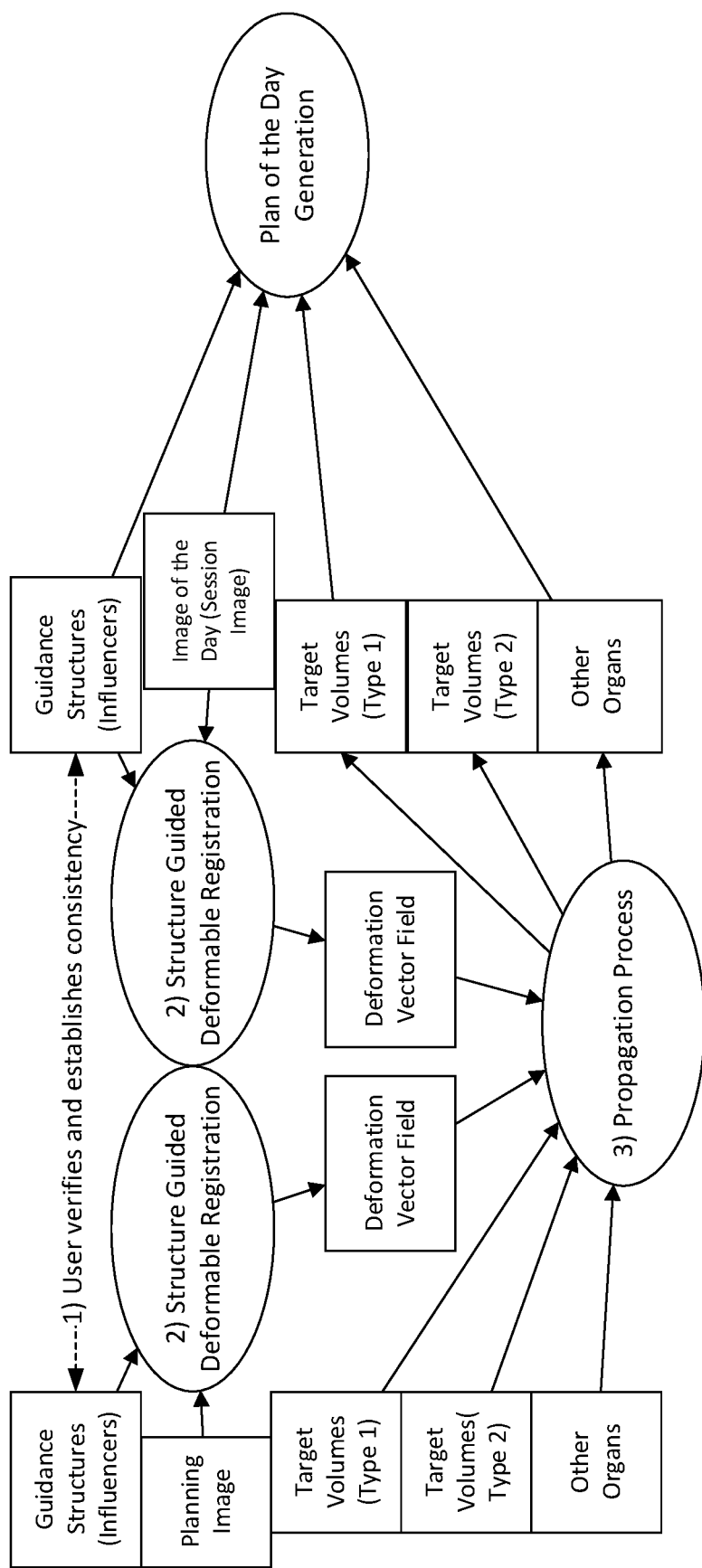
FIG. 12 illustrates an exemplary process using different deformation vector fields to propagate different target volumes, according to various embodiments of the disclosed subject matter.

The exemplary process S100 can also be applied to a planning image 202 as shown in FIG. 12, for example, where the planning image includes a target volume of type 1 and a target volume of type 2, and one or more organs, as well as the guiding structures (i.e., influencers), and a subsequently acquired image, which can be an image acquired during a treatment session. The image of the day also includes the same guiding structures as the planning image. After verifying that the guidance structures in the two images match, one or more structure-guided deformable registration algorithms are applied to deformably register the two images and thereby generate different deformation vector fields (DVFs) that are used to propagate the different target volumes and the one or more organs in the planning image onto the image of the day.

The image of the day, which now includes the contours of all structures, namely, the different target volumes, the one or more organs, and the guidance structures, is then used to generate the plan of the day, which could be different from the plan that was initially planned to be delivered onto the patient 110.

In process S100, the one or more deformation vector fields (DVFs) 222 which propagate the one or more structures in the first set of structures 300 in the planning image 202 can also include partial rigidity deformation constraints so as to enable different points in the first set of structures to deform rigidly, and other points of the same structure in the first set of structures to deform non-rigidly.

Although in the above non-limiting examples, the deformation vector fields (DVFs) were used to propagate structures and contours of target volumes and/or anatomical structures from planning to subsequently acquired image data in connection with radiation therapy, it is to be understood that the determined deformation vector fields (DVFs) additionally, or alternatively, can be used for other applications including non-radiation therapy applications. In general, the determined deformation vector fields (DVFs) can be used in connection with any application in which images are registered.

It is thus apparent that the disclosed subject matter enables the generation of structures in an image using deformable registration techniques that consider the large motions of different structures, as well as the different deformation properties of the structures.

It is also apparent that disclosed subject matter enables the automatic generation of a treatment session image and/or any other image to be used in adaptive radiation therapy or otherwise, which includes all structures from the planning image.

It is also apparent that the disclosed subject matter enables the generation of one or more deformation vector fields (DVF) that allow for the automatic propagation of structures/contours from a pre-treatment (planning) image onto a subsequent image taking into account the large motions of structures as well as the different deformation properties of the propagated structures.

It is also apparent that the disclosed subject matter also enables generating structures in a current image by applying deformable registration between the current image including a structure and a previously generated image that includes the structure and another structure, and applying deformable registration between the two images to propagate the another structure from the previously generated image to the current image using a structure-guided deformable registration algorithm.

It will be appreciated that the aspects of the disclosed subject matter can be implemented, fully or partially, in hardware, hardware programmed by software, software instruction stored on a computer readable medium (e.g., a non-transitory computer readable medium), or any combination of the above.

For example, components of the disclosed subject matter, including components such as a controller, process, or any other feature, can include, but are not limited to, a personal computer or workstation or other such computing system that includes a processor, microprocessor, microcontroller device, or is comprised of control logic including integrated circuits such as, for example, an application specific integrated circuit (ASIC).

Features discussed herein can be performed on a single or distributed processor (single and/or multi-core), by components distributed across multiple computers or systems, or by components co-located in a single processor or system. For example, aspects of the disclosed subject matter can be implemented via a programmed general purpose computer, an integrated circuit device, (e.g., ASIC), a digital signal processor (DSP), an electronic device programmed with microcode (e.g., a microprocessor or microcontroller), a hard-wired electronic or logic circuit, a programmable logic circuit (e.g., programmable logic device (PLD), programmable logic array (PLA), field-programmable gate array (FPGA), programmable array logic (PAL)), software stored on a computer-readable medium or signal, an optical computing device, a networked system of electronic and/or optical devices, a special purpose computing device, a semiconductor chip, a software module or object stored on a computer-readable medium or signal.

When implemented in software, functions may be stored on or transmitted over as one or more instructions or code on a computer-readable medium. The steps of a method or algorithm disclosed herein may be embodied in a processor-executable software module, which may reside on a computer-readable medium. Instructions can be compiled from source code instructions provided in accordance with a programming language. The sequence of programmed instructions and data associated therewith can be stored in a computer-readable medium (e.g., a non-transitory computer readable medium), such as a computer memory or storage device, which can be any suitable memory apparatus, such as, but not limited to read-only memory (ROM), programmable read-only memory (PROM), electrically erasable programmable read-only memory (EEPROM), random-access memory (RAM), flash memory, disk drive, etc.

As used herein, computer-readable media includes both computer storage media and communication media, including any medium that facilitates transfer of a computer program from one place to another. Thus, a storage media may be any available media that may be accessed by a computer. By way of example, and not limitation, such computer-readable media may comprise RAM, ROM, EEPROM, CD-ROM or other optical disk storage, magnetic disk storage or other magnetic storage devices, or any other medium that may be used to carry or store desired program code in the form of instructions or data structures and that may be accessed by a computer.

Also, any connection is properly termed a computer-readable medium. For example, if the software is transmitted from a website, server, or other remote source using a transmission medium (e.g., coaxial cable, fiber optic cable, twisted pair, digital subscriber line (DSL), or wireless technologies such as infrared, radio, and microwave), then the transmission medium is included in the definition of computer-readable medium. Moreover, the operations of a method or algorithm may reside as one of (or any combination of) or a set of codes and/or instructions on a machine readable medium and/or computer-readable medium, which may be incorporated into a computer program product.

One of ordinary skill in the art will readily appreciate that the above description is not exhaustive, and that aspects of the disclosed subject matter may be implemented other than as specifically disclosed above. Indeed, embodiments of the disclosed subject matter can be implemented in hardware and/or software using any known or later developed systems, structures, devices, and/or software by those of ordinary skill in the applicable art from the functional description provided herein.

In this application, unless specifically stated otherwise, the use of the singular includes the plural, and the separate use of "or" and "and" includes the other, i.e., "and/or." Furthermore, use of the terms "including" or "having," as well as other forms such as "includes," "included," "has," or "had," are intended to have the same effect as "comprising" and thus should not be understood as limiting.

Any range described herein will be understood to include the endpoints and all values between the endpoints. Whenever "substantially," "approximately," "essentially," "near," or similar language is used in combination with a specific value, variations up to and including 10% of that value are intended, unless explicitly stated otherwise.

The terms "system," "device," and "module" have been used interchangeably herein, and the use of one term in the description of an embodiment does not preclude the application of the other terms to that embodiment or any other embodiment.

Many alternatives, modifications, and variations are enabled by the present disclosure. While specific examples have been shown and described in detail to illustrate the application of the principles of the present invention, it will be understood that the invention may be embodied otherwise without departing from such principles. For example, disclosed features may be combined, rearranged, omitted, etc. to produce additional embodiments, while certain disclosed features may sometimes be used to advantage without a corresponding use of other features. Accordingly, Applicant intends to embrace all such alternative, modifications, equivalents, and variations that are within the spirit and scope of the present invention.

The invention claimed is:

1. A radiation therapy system comprising:
a computer processing device configured to:
obtain a first image for a subject including a first set of contours, the first set of contours delineating anatomical structures of a first set, and a second set of contours, the second set of contours delineating anatomical structures of a second set, the first and second set of contours being located at respective first locations in the first image, wherein the anatomical structures in the second set include anatomical structures that affect one or more anatomical structures in the first set;
obtain a second image for the subject including the anatomical structures of the second set;
generate contours of the anatomical structures of the second set in the second image, the generated second set of contours in the second image being located at a second location, the second location being different from the first location of the second set of contours in the first image; and
apply image registration to propagate the first set of contours from the first image to the second image, the image registration being guided by the second set of contours, the second image containing, after the propagating, the second set of contours and the propagated first set of contours; and
a radiation therapy device configured to perform a treatment session on the subject based on image data of the second image including the propagated first set of contours and the second set of contours.

2. The radiation therapy system of claim 1, wherein the computer processing device is further configured to determine a treatment plan for the treatment session based on the image data of the second image.

3. The radiation therapy system of claim 1, wherein the computer processing device is configured to propagate the first set of contours
from the first image to the second image by applying a deformable registration algorithm that enables:
creating a first set of contours in the second image;
modifying the first set of contours in the second image based on the second set of contours in the second image;
generating one or more deformation vector fields (DVFs) based on the modifying; and
applying the one or more deformation vector fields (DVFs) to relate the first set of contours from the first image to the second image to generate the first set of contours in the second image.

4. The radiation therapy system of claim 3, wherein the deformable registration algorithm further enables partially rigid deformations of one or more contours within the first set of contours.

5. The radiation therapy system of claim 1, wherein the first set of contours include contours of one or more target volumes and one or more anatomical structures of interest, and the second set of contours include contours of one or more anatomical influencer structures.

6. The radiation therapy system of claim 5, wherein the anatomical influencer structures include anatomical structures that influence one of a shape, size, or location of the one or more target volumes.

* * * * *